US006379961B1

(12) United States Patent
Jessell et al.

(10) Patent No.: US 6,379,961 B1
(45) Date of Patent: *Apr. 30, 2002

(54) USES OF BONE MORPHOGENETIC PROTEINS

(75) Inventors: Thomas M. Jessell; Karel F. Liem, Jr.; Gabi Tremml, all of New York, NY (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/717,175

(22) Filed: Sep. 20, 1996

Related U.S. Application Data

(60) Provisional application No. 60/004,122, filed on Sep. 21, 1995.

(51) Int. Cl.$^7$ .......................... C12N 5/06; A61K 38/22
(52) U.S. Cl. ...................... 435/377; 435/375; 435/368; 514/2; 424/198.1
(58) Field of Search ...................... 514/2, 12; 435/375, 435/368, 377; 424/198.1

(56) References Cited

FOREIGN PATENT DOCUMENTS

WO        WO94/28016        12/1994

OTHER PUBLICATIONS

Basler, K., et al., "Control of cell pattern in the neural tube: regulation of cell differentiation by dosalin–1: a novel TGF family member." 1993, *Cell* 73: 687–702.
Dickinson, M.E., et al., "Dorsalization of the neural tube by the non–neural ectoderm." 1995, *Development* 121: 2099–2106.
Ericson, J., et al., "Sonic hedgehog induces the differentiation of ventral forebrain neurons: a common signal for ventral patterning along the rostrocaudal axis for the neural tube." 1995 *Cell* 81: 747–756.
Fainsod, A., et al., "On the function of BMP–4 in patterning the marginal zone of the Xeonpus embryo." 1994, *Embo J.* 13: 5015–5025.
Graham, A., et al., "The signaling molecule BMP–4 mediates apoptosis in the rhombencephalic neural crest." 1994, *Nature* 372: 684–686.
Houston, B., et al., "Molecular cloning and expression of bone morphogenetic protein 7 in the chick epiphyseal growth plate." 1994, *J. Mol. Endocrinol.* 13: 289–301.

Jones, C.M., et al., "Involvement of bone morphogenetic protein–4 (BM–4) and Vgr–1 in morphogenesis protein–4 (BMP–4) and VGR–1 and neurogenesis in the mouse." 1991, *Development* 11: 531–542.
Liem, K.F., et al., "Dorsal differentiation of neural plate cells induced by BMP–mediated signals from epidermal ectoderm." 1995, *Cell* 82: 969–979.
Moury, J. and Jacobson, A., "The origins of neural crest cells in the axolotl." 1990, *Dev. Biol.* 141: 243–253.
Placzek, M., et al., "Induction of floor plate differentiation by contact–dependent, homogenetic signals." 1993, *Development* 117: 205–218.
Roelink, H., et al., "Floor plate and motor neuron induction by vhh–1, a vertebrate homolog of hedgehog expressed by the notochord " 1994, *Cell* 76: 761–775.
Roelink, H., et al., "Floor plate and motor neuron induction by different concentrations of the amino terminal cleavage product of sonic hedgehog autoproteolysis." 1995, *Cell* 81: 445–455.
Selleck, M. and Bronner–Fraser, M., "Origins of the avian neural crest: the role of neural plate–epidermal interactions." 1995, *Development* 121: 525–538.
Tanabe, Y., et al., "Induction of motor neurons by sonic hedgehog is independent of floor plate differentiation." 1995, *Current Biology* 5: 651–658.
Van Straaten, H.M.W. and Kekking, J.W.M., "Development of floor plate neurons and axonal outgrowth pattern in the early spinal cord of the notochord–deficient chick embryo." 1991, *Anat. Embryol.* 184: 53–63.
Yamada, T., et al., "Control of cell pattern in the developing nervous system: polarizing activity of the floor plate and notochord." 1991, *Cell* 64: 635–647.
Yamada, T., et al., "Control of cell pattern in the neural tube: motor neuron induction by diffusible factors from notochord and floor plate." 1993, *Cell* 73: 673–686.
Marieb, In "Human Anatomy and Physiology, second edition" (1992) The Benjamin/Cummings Publishing Company, Inc., Redwood City, CA, pp. 373–379.*
Jackowski Bartish J. of Neurosurgery 9 (1995) 303–317.*
Wehby et al. Society for Neuroscience Abstracts 19 (1993) 1727.*

* cited by examiner

*Primary Examiner*—Gary L. Kune
*Assistant Examiner*—Robert C. Kayes
(74) *Attorney, Agent, or Firm*—John P. White; Cooper & Dunham LLP

(57) ABSTRACT

This invention provides a composition comprising an amount of a purified protein selected from a group consisting of bone morphogenetic protein 4, bone morphogenetic protein, bone morphogenetic protein 7, dorsalin–1 and combinations thereof effective to stimulate neural crest cell differentiation and an acceptable carrier. This invention provides different uses of this composition.

1 Claim, 23 Drawing Sheets

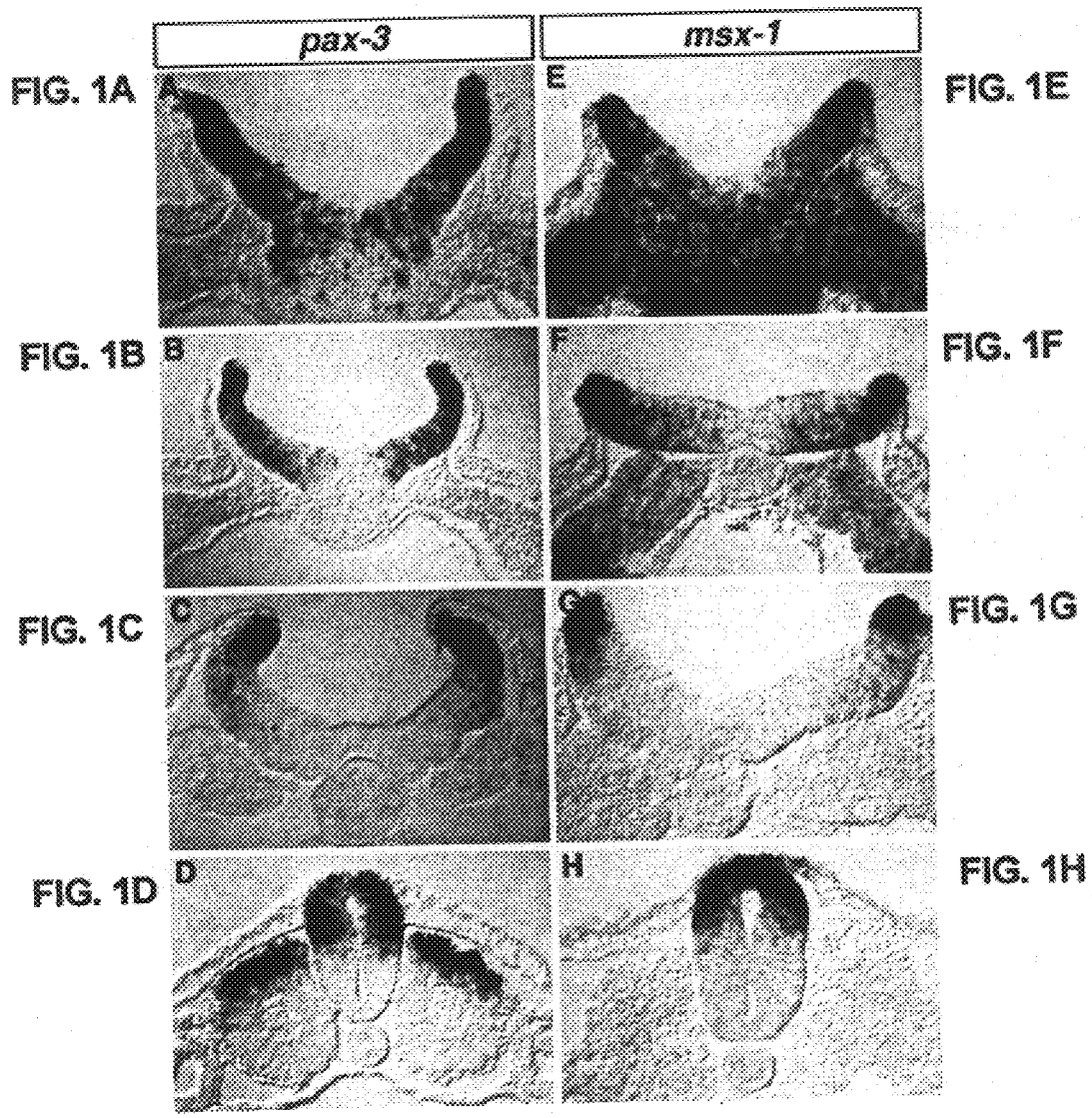

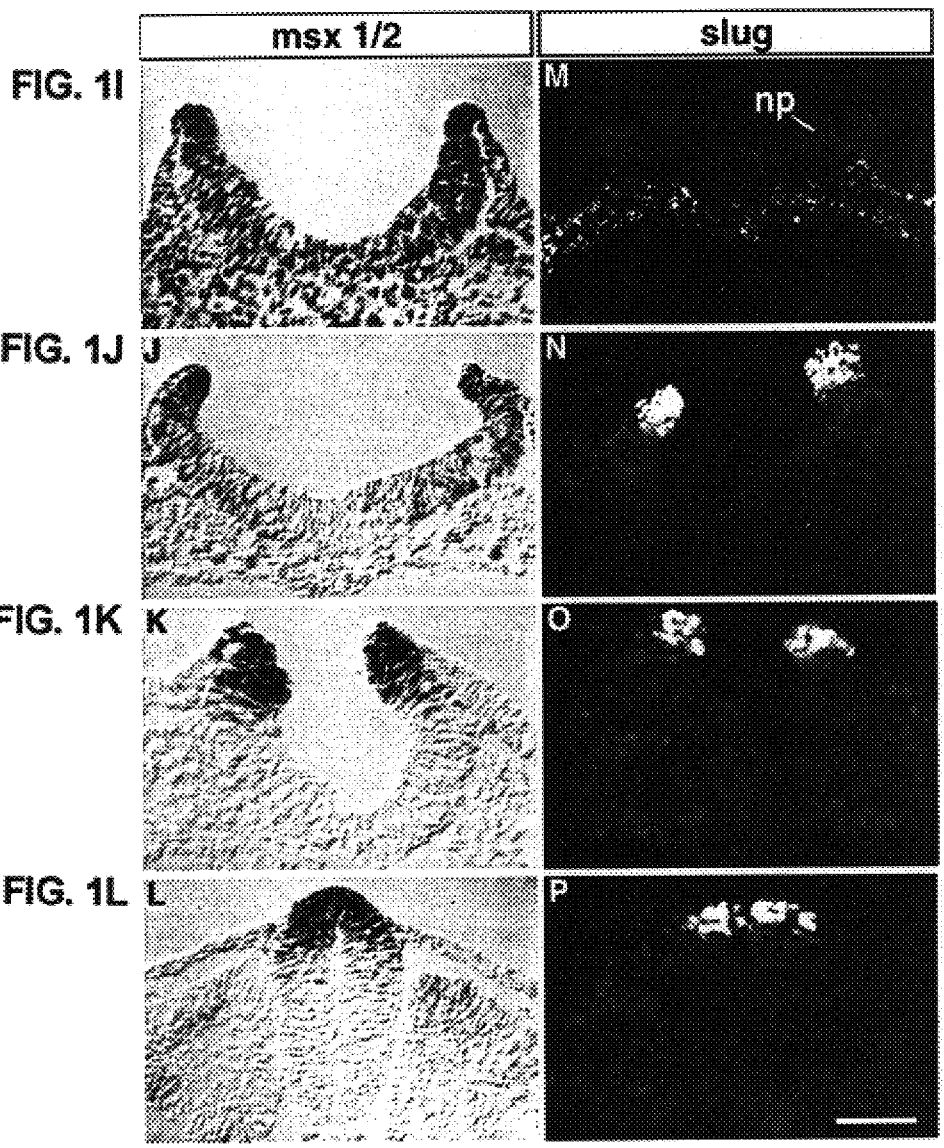

A Expression of pax3 and dsl

B Induction by ectoderm

C Induction by BMPs

D Repression by notochord and SHH

FIG. 3A | FIG. 3B | FIG. 3C
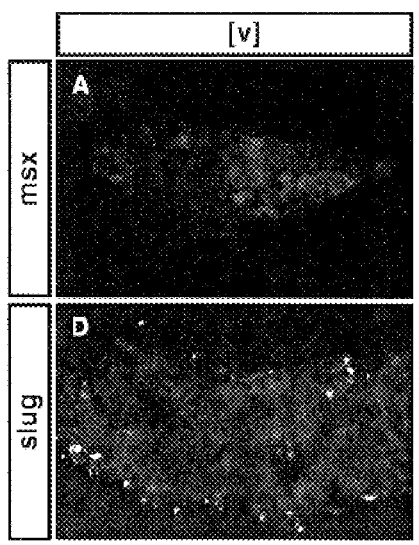 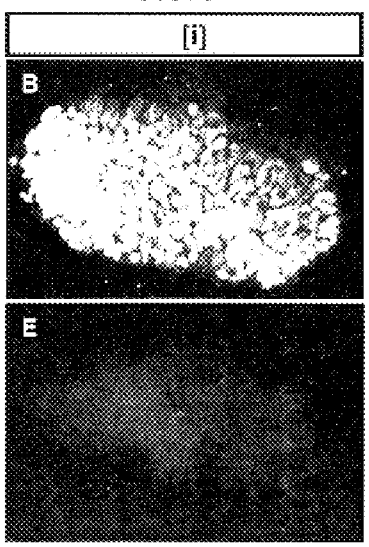 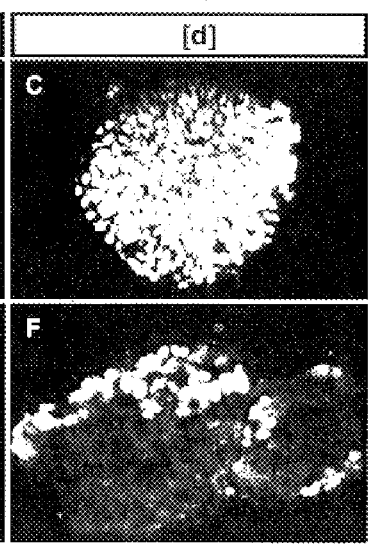
FIG. 3D | FIG. 3E | FIG. 3F FIG. 3G [v]
FIG. 3H [i]
FIG. 3I [d]
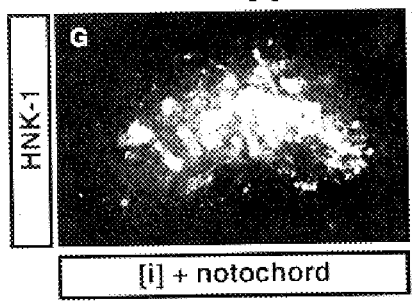 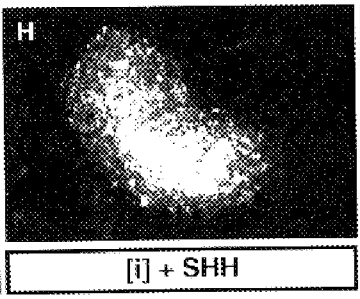 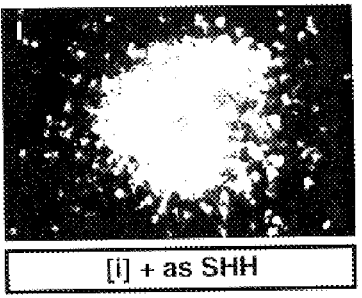
[i] + notochord
[i] + SHH
[i] + as SHH
 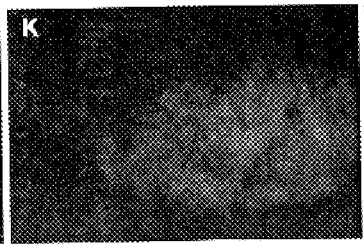 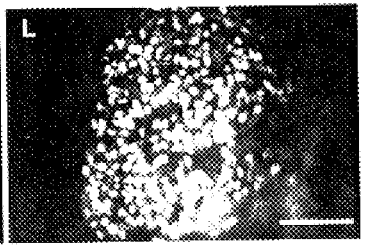
FIG. 3J
FIG. 3K
FIG. 3L

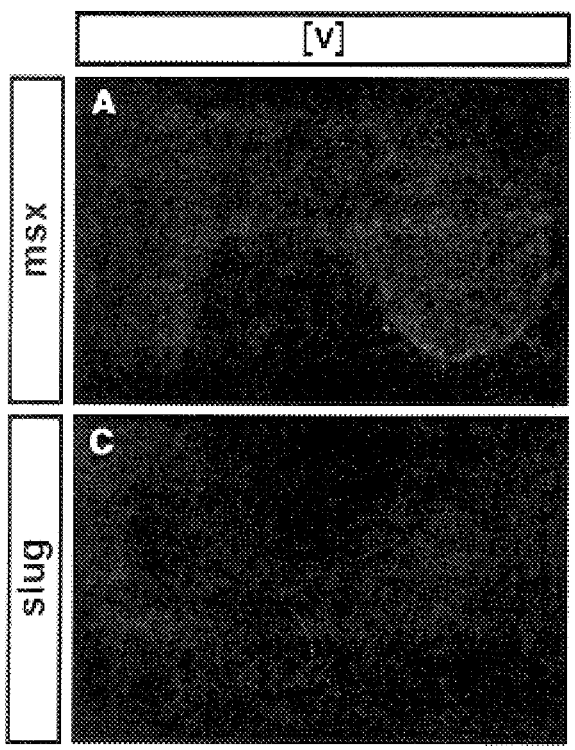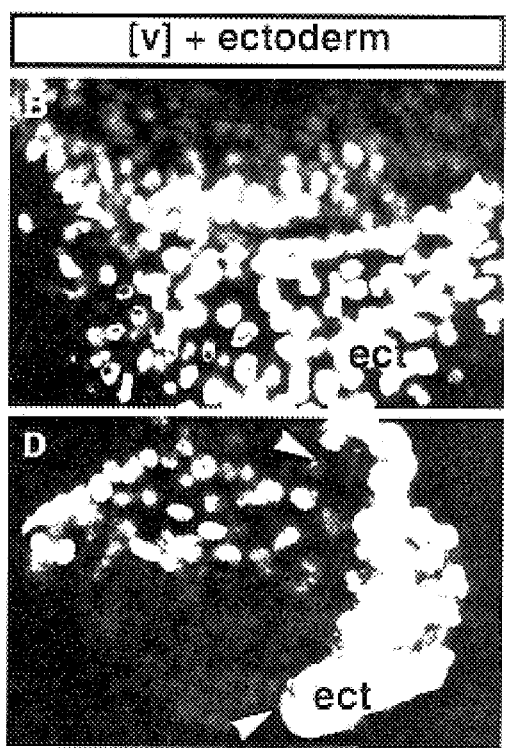
FIG. 4A  FIG. 4B
FIG. 4C  FIG. 4D

FIG. 4E  FIG. 4F  FIG. 4G
[v]  [v] + ectoderm
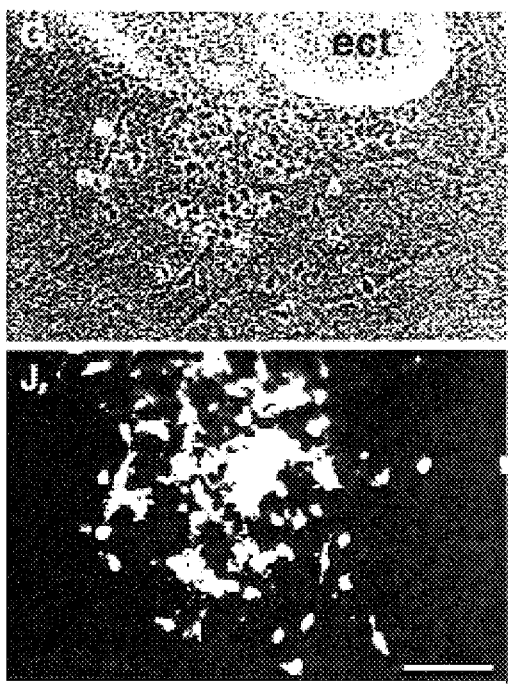
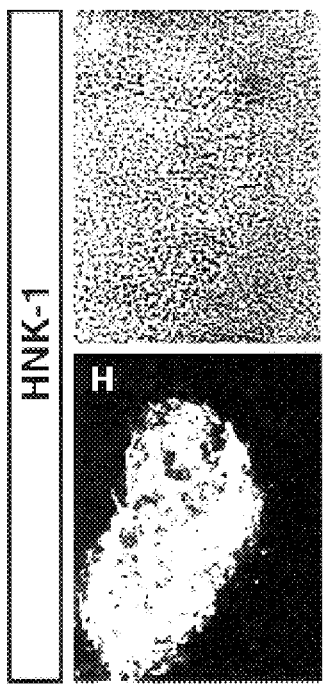
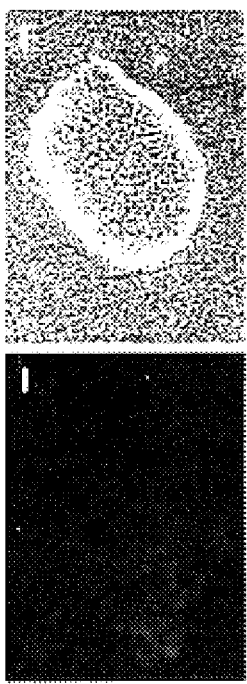
FIG. 4H  FIG. 4I  FIG. 4J

BMP-4

BMP-7

FIG. 6A  FIG. 6B  FIG. 6C
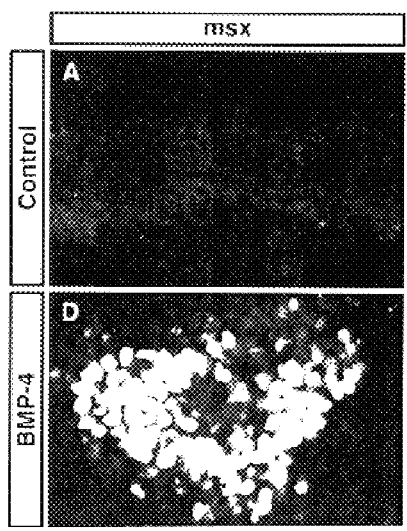
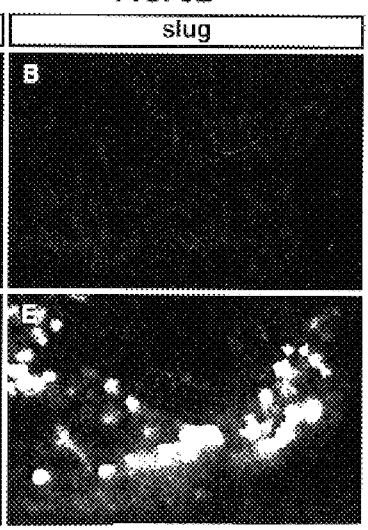
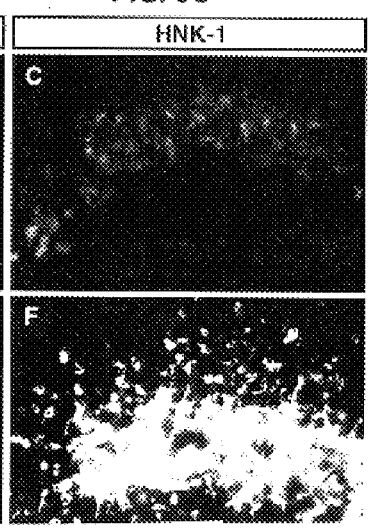
FIG. 6D  FIG. 6E  FIG. 6F FIG. 6G
msx
FIG. 6H
slug
FIG. 6I
HNK-1
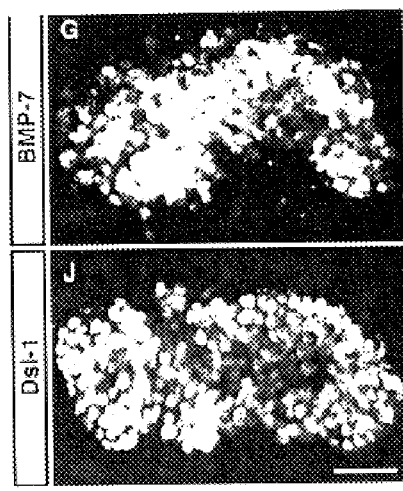 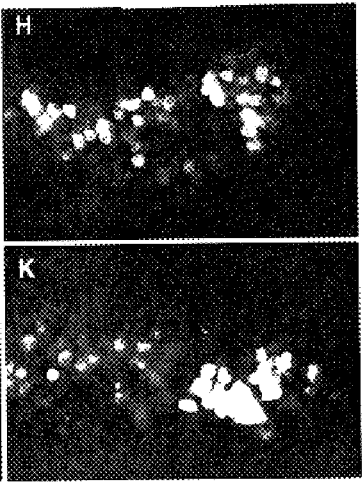 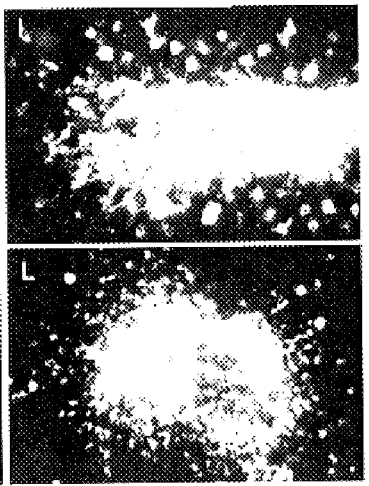
FIG. 6J
FIG. 6K
FIG. 6L

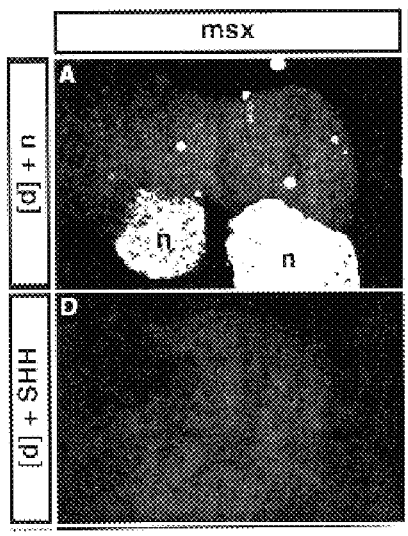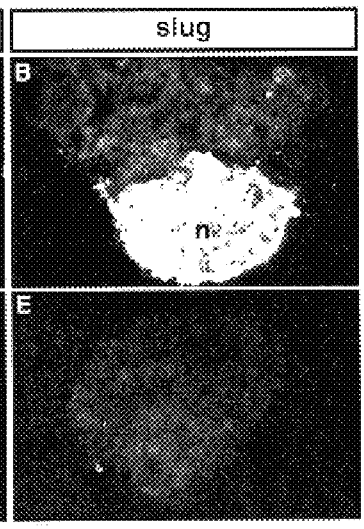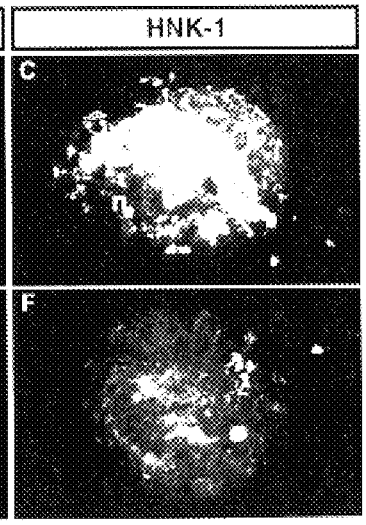
FIG. 7A  FIG. 7B  FIG. 7C
FIG. 7D  FIG. 7E  FIG. 7F FIG. 7G
msx
FIG. 7H
slug
FIG. 7I
HNK-1
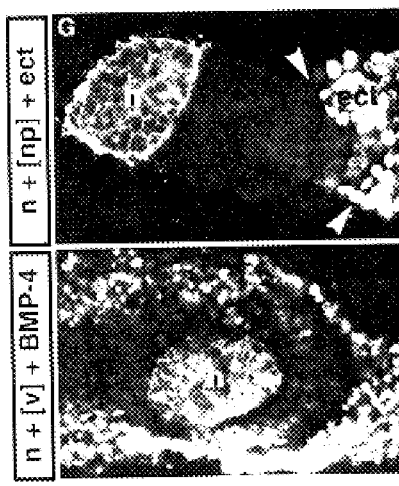
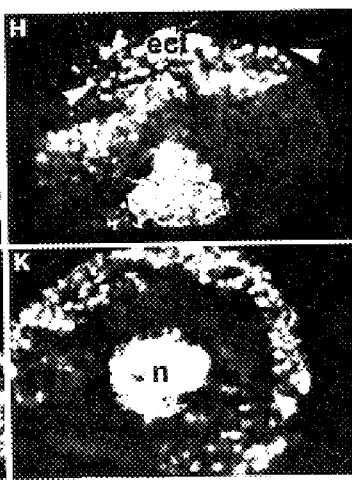
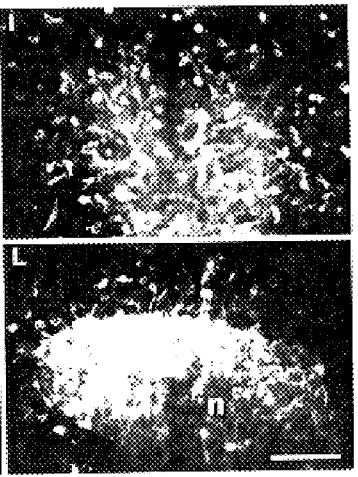
FIG. 7J
FIG. 7K
FIG. 7L

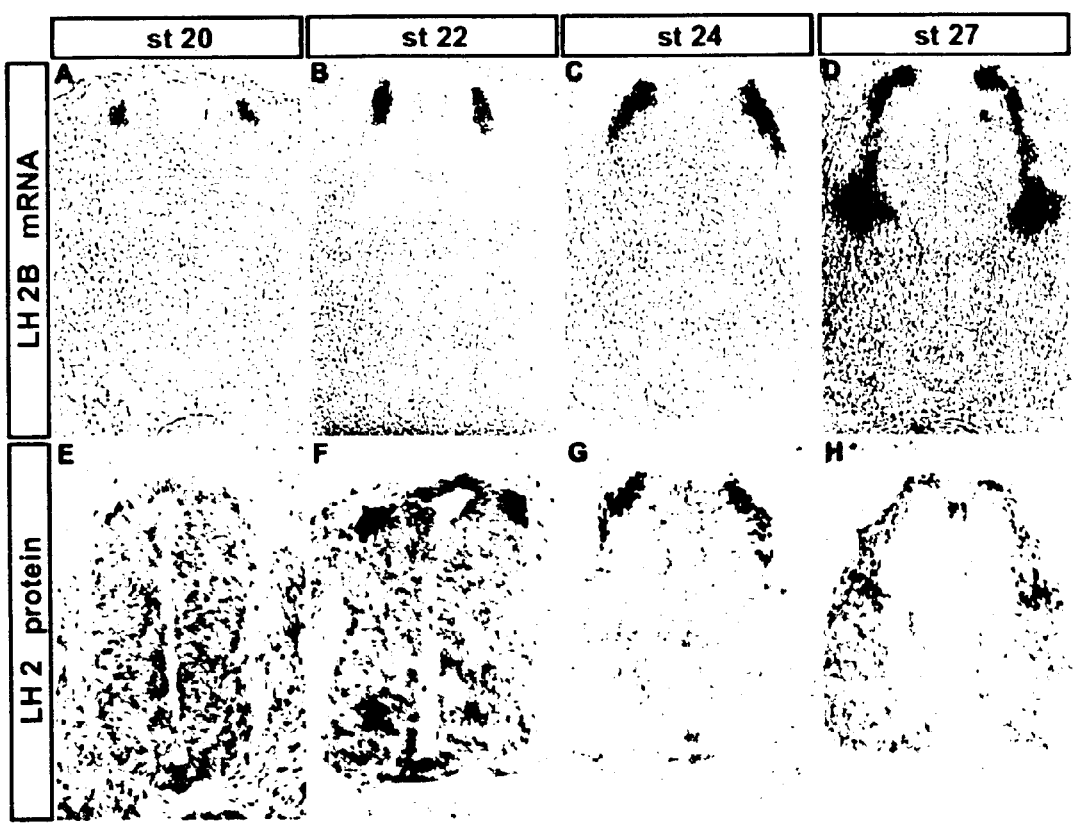

FIG. 10I  FIG. 10J  FIG. 10K  FIG. 10L
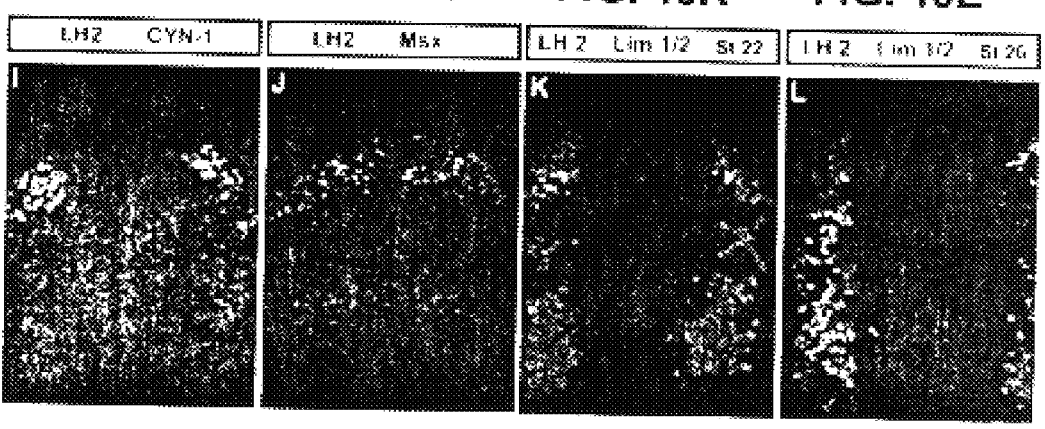
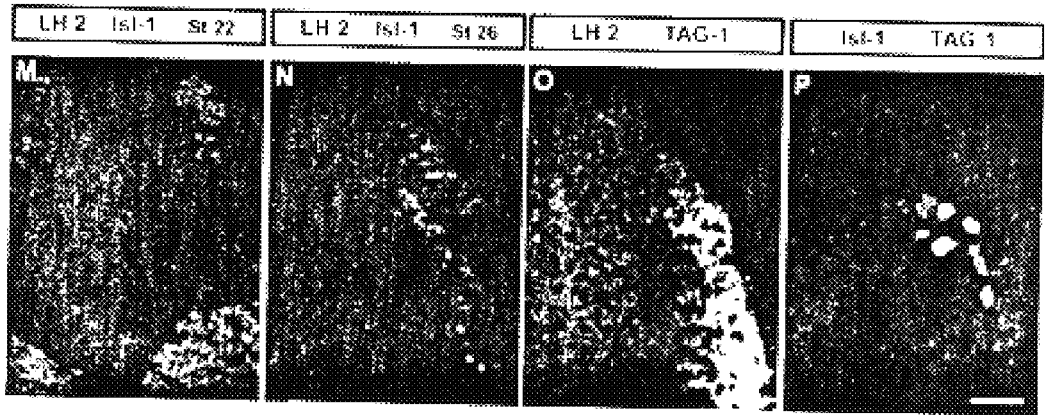
FIG. 10M  FIG. 10N  FIG. 10O  FIG. 10P

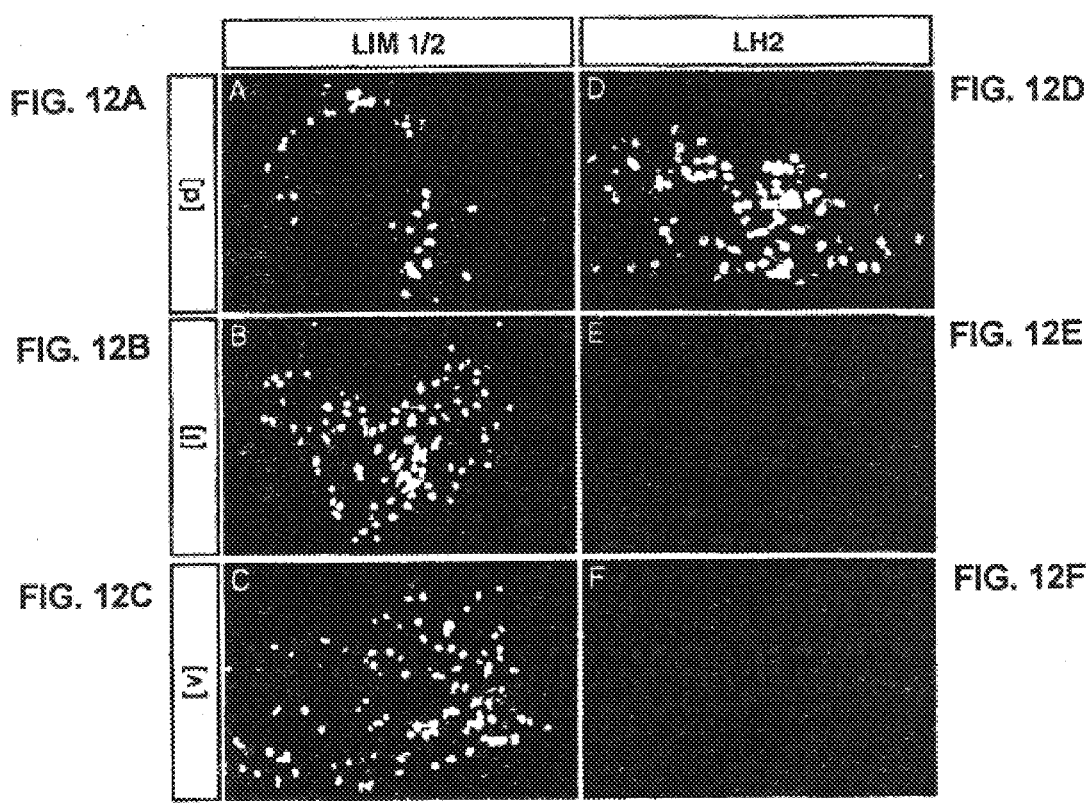

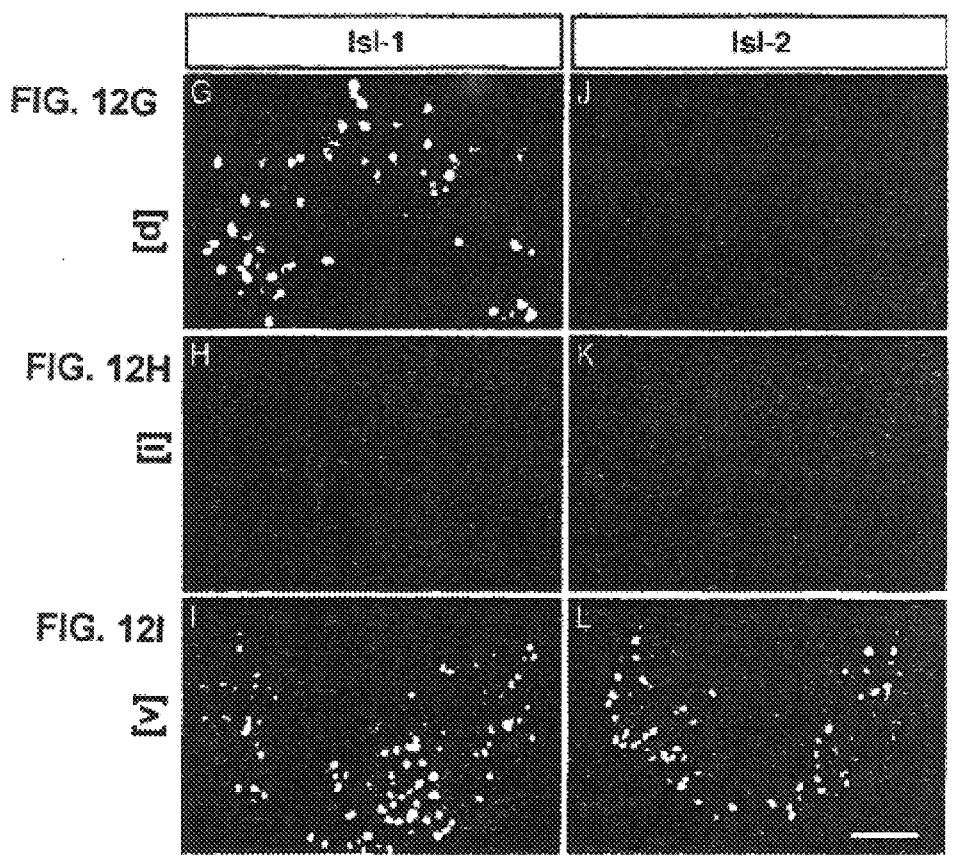

USES OF BONE MORPHOGENETIC PROTEINS

This application claims the benefit of U.S. Provisional Application No. 60/004,122, filed Sep. 21, 1995, the content of which is hereby incorporated into this application by reference.

BACKGROUND OF THE INVENTION

Throughout this application, various references are referred to by abbreviation. Disclosures of these publications in their entireties are hereby incorporated by references into this application to more fully describe the state of the art to which this invention pertains. Full bibliographic citation for these references may be found at the end of the specification, preceding the claims.

The cellular interactions that control the differentiation of dorsal cell types form neural progenitors have been examined in neural plate explants. Certain genes that are expressed in the dorsal neural tube are initially expressed uniformly within the neural plate and appear to achieve their dorsal restriction through a Sonic Hedgehog (SHH)-mediated repressive signal from the notochord. The acquisition of definitive dorsal cell fates, however, requires a contact-dependent signal from the epidermal ectoderm. BMP-4 and BMP-7 are expressed in the epidermal ectoderm and both proteins mimic its inductive activity. BMP-4 and a related gene, Dsl-1, are subsequently expressed by cells in the dorsal neural tube, indicating that the early dorsalizing activity of the epidermal ectoderm is later acquired by neural cells. The differentiation of dorsal cell types, therefore, appears to be initiated at the neural plate stage and to involve the opponent activities of a BMP-mediated dorsalizing signal from the epidermal ectoderm and a SHH-mediated ventralizing signal from the notochord.

The diverse neuronal and glial cell types generated during the development of the vertebrate nervous system derive from a simple columnar epithelium, the neural plate. The differentiation of distinct cell types from neural plate progenitors is thought to be controlled by the actions of secreted inductive factors (Smith, 1994; Johnson and Tabin, 1995). Cell types generated from the medial region of neural plate (notably floor plate cells and motor neurons) populate the ventral half of the neural tube and are induced by Sonic Hedgehog (SHH), a secreted glycoprotein that is synthesized by axial mesodermal cells of the notochord (Echelard et al, 1993; Krauss et al., 1993; Ericson et al., 1995; Marti et al., 1995; Roelink et al., 1994, 1995; Tanabe et al., 1995). Elimination of the notochord prevents the differentiation of floor plate cells and motor neurons (van Straaten and Hekking, 1991: Yamada et al., 1991; Ericson et al, 1992) establishing that a signal from the notochord, presumably SHH, is required for the differentiation of ventral cell types.

Cell types derived from the lateral region of the neural plate which populate the dorsal half of the neural tube (neural crest cells, dorsal commissural neurons and roof plate cells) are able to differentiate in the absence of notochord-derived signals (Yamada et al., 1991; Ericson et al., 1992; Tremml et al., unpublished data). Moreover, in the absence of the notochord certain genes that are normally restricted to dorsal regions of the neural tube are expressed at all dorsoventral levels (Yamada et al., 1991, Basler et al., 1993; Goulding et al, 1993). These observations raise the issue of how the dorsal fates of neural plate cells are acquired. One possibility is that neural plate cells are predisposed to differentiate into dorsal cell types unless exposed to a ventralizing signal from the notochord. Alternatively, the acquisition of dorsal fates might require the action of inductive signals that originate from adjacent tissues. Evidence for the existence of dorsalizing signals has derived from the analysis of neural crest cell differentiation. Epidermal ectoderm cells that flank the neural plate and mesodermal cells that underly the lateral border of the neural plate have each been proposed as sources of signals that induce neural crest cells (Moury and Jacobson, 1989, 1990; Takada et al., 1994; Dickinson et al., 1995; Selleck and Bronner-Fraser, 1995; Mayor et al., 1995; de la Torre and Tessier-Lavigne, unpublished data). Neural crest cells can be induced in vitro by exposure of neural plate explants to Dorsalin-1 (Dsl-1), a TGF(-related factor (Kingsley, 1994) expressed in the dorsal region of the neural tube (Basler et al., 1993). Dsl-1 is, however, not expressed in the epidermal ectoderm and appears in the neural tube only after neural crest cells have been specified (Basler et al., 1993; Nieto et al., 1994; Nakagawa and Takeichi, 1995) indicating that Dsl-1 is not involved in the initial steps of neural crest cell differentiation. Thus, the cellular interactions that initiate the dorsal differentiation of neural plate cells and the molecular identity of relevant inducing factors remain uncertain.

In the present studies applicants have analyzed the interactions that specify the dorsal fate of neural plate cells using an in vitro assay of cell differentiation in neural plate explants. Applicants first examined whether neural plate cells are predisposed to dorsal fates or whether inductive signals from adjacent cells are required. Applicants' results show that certain genes that characterize the dorsal neural tube are initially expressed by all neural plate cells and achieve their dorsal restriction through a SHH-mediated repressive signal from the notochord. The acquisition of definitive dorsal cell fates, however, does not occur by default and instead involves a contact-dependent inductive signal from the epidermal ectoderm. Two members of the TGF gene family, BMP-4 and BMP-7, are expressed in the epidermal ectoderm flanking the neural plate and recombinant BMP-4 and BMP-7 mimic the dorsalizing activity of the epidermal ectoderm. The acquisition of dorsal neural fates is, therefore, initiated at the neural plate stage and appears to involve the opponent activities of a BMP-mediated dorsalizing signal from the epidermal ectoderm and a SHH-mediated ventralizing signal from the notochord.

SUMMARY OF THE INVENTION

This invention provides a composition for stimulating neural crest cell differentiation comprising an amount of a purified protein selected from a group consisting of bone morphogenetic protein 4, bone morphogenetic protein 5, bone morphogenetic protein 7, dorsalin-1 and combinations thereof effective to stimulate neural crest cell differentiation and an acceptable carrier. This invention also provides methods for stimulating neural crest cell differentiation in a culture comprising administering the above composition to the culture. This invention provides a method for stimulating neural crest cell differentiation in a subject comprising administering to the subject the above composition.

This invention provides a composition for regenerating nerve cells in a subject comprising an amount of a purified protein selected from a group consisting of bone morphogenetic protein 4, bone morphogenetic protein 5, bone morphogenetic protein 7, dorsalin-1and combinations thereof effective to regenerate nerve cells and an acceptable carrier. This invention provides a method for regenerating nerve cells in a subject comprising administering to the subject the above composition.

This invention also provides a composition for promoting bone growth in a subject comprising an amount of the purified protein selected from a group consisting of bone morphogenetic protein 4, bone morphogenetic protein 5, bone morphogenetic protein 7, dorsalin-1 and combinations thereof effective to promote bone growth and an acceptable carrier. This invention further provides methods for promoting bone growth in a subject comprising administering to the subject the above composition.

This invention provides a composition for promoting wound healing in a subject comprising an amount of the purified protein selected from a group consisting of bone morphogenetic protein 4, bone morphogenetic protein 5, bone morphogenetic protein 7, dorsalin-1 and combinations thereof effective to promote wound healing and an acceptable carrier. This invention also provides methods for promoting wound healing in a subject comprising administering to the subject the above composition.

This invention provides a composition for treating neural tumor in a subject comprising an amount of the purified protein selected from a group consisting of bone morphogenetic protein 4, bone morphogenetic protein 5, bone morphogenetic protein 7, dorsalin-1 and combinations thereof effective to inhibit neural tumor cell growth and an acceptable carrier. This invention also provides methods for treating neural tumor in a subject comprising administering to the subject the above composition.

BRIEF DESCRIPTION OF THE FIGURES

FIGS. 1A–P. Expression of pax-3 and msx-1 and slug in the neural plate and neural tube.
Panels show the distribution of pax-3 (A–D) msx-1 (E–H), msx proteins (I–L) and slug protein (M–P) in the neural plate and neural tube of stage 10 chick embryos.
A, E, I, M: Sections through the neural plate rostral to Hensen's node. Expression of pax-3 (A) msx-1 (E) and msx proteins (I) in neural plate cells. Slug is not expressed in the neural plate at this level (M).
B, F, J, N: Sections through a more rostral level of the neural plate. Expression of pax-3 (B), msx-1 (F), msx proteins (J) is not detectable in cells at the midline of the neural plate. Slug is expressed by cells in the lateral region of the neural plate (N).
C, G, K, 0: Sections through the neural fold. Expression of pax-3 (C), msx-1 (G) and msx proteins (K) is restricted to the dorsal region of the neural folds. Slug (O) is expressed by dorsal cells.
D, H, L, P: Sections through the neural tube. Expression of pax-3 (D), msx-1 (H), msx proteins (L) and slug (P) is restricted to the dorsal neural tube.
Scale bar=100 um.

FIGS. 3A–L. Msx, slug and HNK-1 Expression in Neural Plate Explants
Msx and slug expression was assayed after 18 h and migratory HNK-$1^+$ cells after 40 h.
A–C: Ventral neural plate explants express few if any msx$^+$ cells (2±1 cells/section, mean±s.e.m., n=6) (A). Msx is expressed by over 90% of cells in intermediate neural plate explants (61±3 cells/section, mean±s.e.m., n=6) (B) and dorsal neural plate explants (68±5 cells/section, n=6) (C).
D–F: Slug$^+$ cells are absent from ventral (D) and intermediate (E) but present in dorsal (F) neural plate explants. Sections of dorsal neural plate explants contained 39±4 slug$^+$ cells/section (n=10).
G–I: Migratory HNK-$1^+$ cells are absent from ventral (G) and intermediate (H) but present in dorsal (I) neural plate explants (56±6 migratory HNK-$1^+$ cells/explant; n=24). Slug expression was not detected in migratory HNK-$1^+$ cells (not shown).
J: Neural cells in a conjugate of intermediate neural plate explant and notochord (n) do not express msx. The notochord explant is detected with Mab Not-1.
K: No msx$^+$ cells are detected in intermediate neural plate explants grown in vitro on COS cells transfected with sense rat Shh.
L: Msx is expressed by most cells in intermediate neural plate explants grown in vitro on COS cells transfected with antisense rat Shh.
Similar results were obtained in at least 12 explants.
Scale bar: A–F, J–L=80 m, G–I=100 m FIGS. 4A–J. Induction of msx, slug and HNK-$1^+$ cells by Epidermal Ectoderm.
A: Section through a ventral neural plate explant grown in culture for 18 h. No msx$^+$ cells are detected.
B: Section through a ventral neural plate explant grown for 18 h in contact with epidermal ectoderm isolated from a stage 10 quail embryo. The section was labeled with antibodies directed against msx (nuclear) and the quail-specific perinuclear marker QCPN. The border between the quail ectoderm (ect) and chick neural plate tissue is marked with arrowheads. Msx$^+$ cells (55±8 cells/section; n=3) are detected in the chick neural plate explant close to the border with the quail ectoderm.
C: Ventral neural plate explant grown alone. No slug$^+$ cells are detected.
D: Ventral neural plate explant grown in contact with stage 10 quail epidermal ectoderm, labeled with anti-msx and QCPN antibodies. Slug$^+$ cells (16±3 cells/section, n=8) are induced. The junction of the neural and ectodermal (ect) explants is shown by arrowheads. Ectodermal tissue is located close to the region of slug$^+$ cells.
E, H: Ventral neural plate explant grown alone in culture for 40 h. Cells in the explant express HNK-1 but there are no migratory HNK-$1^+$ cells
F, I: Chick epidermal ectodermal explant grown alone in culture for 40 h. No HNK-1 expression is detected.
G, J: Conjugate of ventral neural plate and epidermal ectoderm explants, grown in culture for 40 h. HNK-$1^+$ cells (38±5 cells/explant; n=10) have migrated from the neural plate explant.
Images are representative of at least 10 explants.
Scale bar: A–D=30 m, E–J=100 m.

FIGS. 5A–H. Expression of BMP-4 and BMP-7 in Epidermal Ectoderm and Dorsal Neural Tube.

Figure 2A:
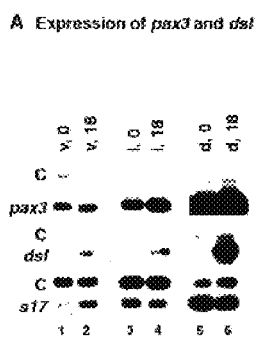
FIGS. 2A–D. RT-PCR Analysis of pax-3, Dsl-1 and S17 Expression in Neural Plate Explants
In all lanes, upper bands (C) indicate competitive RNA templates lower bands, tissue-derived transcripts. Grouped lanes are from the same experiment. The chick S17 gene was used as an internal control for the amount of tissue.
In C, BMP-4 and BMP-7 were added in the form of COS cell conditioned medium diluted 1:2 in F12 medium. Dsl-1 was added at $3 \times 10^{-11}$ M. In D, conditioned medium containing amino terminal SHH was added at a concentration of $\sim 10^{-8}$ M.
Abbreviations; v: ventral neural plate explant; d: dorsal neural plate explant; SHH: Sonic Hedgehog; n:notochord; ect:epidermal ectoderm; Dsl-1: Dorsalin-1. Numbers above lanes indicate culture time, in hours. Each lane is representative of at least three different experiments.

The distribution of BMP-4 and BMP-7 was determined by in situ hybridization analysis of stage 10 chick embryos.

A, B: Sections of the neural plate at a level rostral to Hensen's node. BMP-4 (A) and BMP-7 (B) are expressed in the epidermal ectoderm adjacent to the neural plate. No expression is detected in the neural plate.

C, D; Sections of the neural plate at a more rostral level showing a restriction BMP-4 expression (C) to the ectoderm flanking the neural plate and to the dorsal folds of the neural plate. BMP-7 expression (D) is maintained in the epidermal ectoderm.

E, F: Sections through the neural tube showing high levels of BMP-4 expression (E) in the dorsal midline of the neural tube and in overlying midline ectoderm. BMP-7 expression (F) has disappeared from the epidermal ectoderm but is expressed at low levels in the dorsal neural tube.

G, H: Sections through the neural tube at prospective forebrain level showing BMP-4 expression (G) by cells at the dorsal midline of the neural tube but not in the epidermal ectoderm. BMP-7 is expressed (H) at high levels in the epidermal ectoderm but not in the neural tube.

Scale bar: A–D=80 m, E–H=100 m.

FIGS. 6A–L. Induction of msx, slug and HNK-$1^+$ cells

A–C: Ventral neural plate explants exposed to medium from COS cells transfected with a truncated Dsl-1 construct do not contain msx$^+$ cells (A), slug$^+$ cells (B) or give rise to migratory HNK-$1^+$ cells (C).

D–F: Ventral neural plate explants grown in medium derived from BMP-4 transfected COS cells contain msx$^+$ cells (71±5 cells/section, n=6) (D), slug$^+$ cells, (26±2 cells/section, n=6) (E) and give rise to migratory HNK-$1^+$ cells (49±5 cells/explant; n=10) (F).

G–I: Ventral neural plate explants grown in medium derived from BMP-7-transfected COS cells contain msx$^+$ cells (100±6 cells/section; n=6) (G), slug$^+$ cells (18±3 cells/section; n=10) (H) and give rise to migratory HNK-$1^+$ cells (88±15 cells/explant; n=4) (I).

J–L: Ventral neural plate explants grown in the presence of $3 \times 10$–11 M Dsl-1 contain msx$^+$ cells (86±3 cells/section; n=5) (J), slug$^+$ cells (33±2 cells/section; n=7) (K) and give rise to migratory HNK-$1^+$ cells (65±20 cells/explant; n=5) (L).

Each image is representative of at least 4 explants.

Scale bar: A–K=80 m, L=130 m.

FIGS. 7A–L. Inductive Activities of Epidermal Ectoderm and BMPs Oppose those of Notochord and SHH.

A–C: Dorsal neural plate explants grown for 18 h in contact with notochord (n) contain few msx$^+$ cells (A). Dorsal neural plate explants grown in contact with notochord contain few slug$^+$ cells (4±2 cells/section; n=10) (B) and at 40 h gave rise to few migratory HNK-$1^+$ cells (11±6 cells/section; n=9) (C)

D–F: Dorsal neural plate explants grown in the presence of medium containing the amino terminal cleavage product of SHH (~$10^{-8}$ M) for 18 h did not contain msx$^+$ cells (D), contained few slug$^+$ cells (1±0.3 cells/section; n=10) (E) and gave rise at 40 h, to few migratory HNK-$1^+$ cells (16±4 cells/explant; n=10) (F).

G: Intermediate neural plate explants grown for 18 h in contact with notochord (n) and quail epidermal ectoderm (ect). Msx$^+$ cells (22±4 cells/section; n=3) are detected in the neural plate explant close to the epidermal ectoderm. Ectodermal cells are labelled by QCPN. The notochord explant (n) is labeled with Not-1.

H: Dorsal neural plate explants grown for 18 h in contact with notochord (n) and quail epidermal ectoderm. Slug$^+$ cells (16±4 cells/section; n=6) are detected in the neural plate explant close to the ectoderm. The border between the ectodermal and neural explants is shown by arrowheads.

I: Dorsal neural plate explant grown for 40 h in contact with notochord (n) and chick epidermal ectoderm shows migratory HNK-$1^+$ cells (45±11 cells/explant; n=7).

J: Ventral neural plate explant grown for 18 h in contact with notochord in the presence of medium from BMP-4-transfected COS cells (1:2 dilution). Msx$^+$ cells (84±10 cells/section; n=4) are detected in the region of the explant furthest from the notochord.

K: Ventral neural plate explant grown for 18 h in contact with notochord in the presence of medium from BMP-4-transfected COS cells (1:2 dilution). Most slug$^+$ cells (34±10 cells/section; n=4) are detected in the region of the explant furthest from the notochord.

L: Ventral neural plate explant grown for 40 h in contact with notochord (n) in the presence of BMP-4. Numerous HNK-$1^+$ cells (45±11 cells/explant; n=7) have migrated from the explant on the side furthest from the notochord (n).

Images are representative of 4–12 explants.

Scale bar=80 m

FIGS. 8A–F. Expression of Multiple BMPs by Roof Plate Cells in Embryonic Chick Spinal Cord. Images show localization of BMP mRNAs in sections of stage 20 or stage 24 spinal cord.

A. BMP-4 mRNA is restricted to the roof plate of the spinal cord at stage 20. Note that expression of BMP-4 by the overlying ectoderm apparent at stage 10 (Liem, 1995) is absent by this stage.

B. BMP-4 mRNA is restricted to the roof plate of the spinal cord at stage 24.

C. BMP-2 mRNA is not expressed in the spinal cord at stage 24. BMP-2 mRNA is absent between stages 10 to 24 (data not shown).

D. BMP-5 mRNA expression is restricted to the roof plate of the spinal cord at stage 24. Expression in mesenchymal cells adjacent to the dorsal spinal cord is also detected at this stage. BMP-5 is expressed in the roof plate between steps 18–24 (not shown).

E. BMP-7 mRNA is expressed in the roof plate of the spinal cord at stage 24 and also at lower levels in cells in the ventricular zone of the dorsal spinal cord. BMP-7 mRNA is expressed in the roof plate between stages 18–24 (not shown).

F. Dsl-1 mRNA is expressed at high levels in the roof plate at stage 24 and at much lower levels in a small group of dorsal ventricular zone cells.

Scale bar=um

Figure 9B:
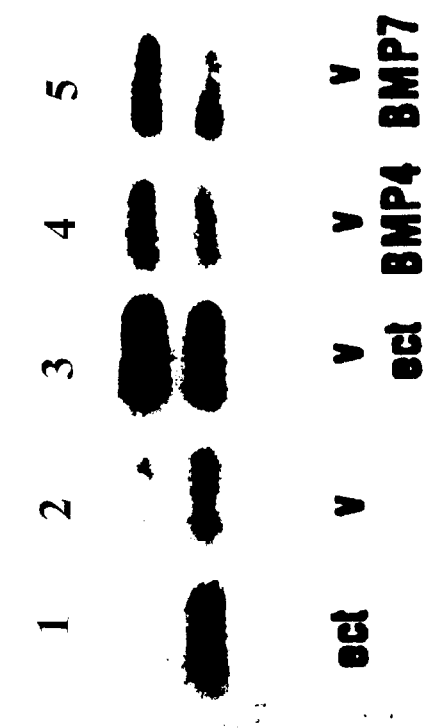
Figure 9A:
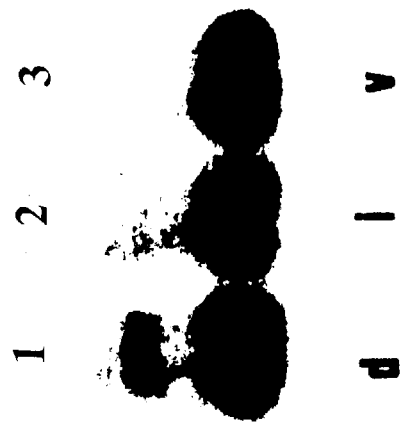

FIGS. 9A–B. Induction of BMP-4 Expression in Neural Plate Explants by Epidermal Ectoderm and BMPs A. BMP-4 expression in explants isolated from prospective dorsal (d), intermediate (i), and ventral (v) regions of stage 20 neural plate. Dorsal but not intermediate or ventral explants express BMP-4 mRNA at this stage.

B. lane 1: RT-PCR analysis of chick BMP-4 does not detect transcripts in E_11 rate epidermal ectoderm (ect). BMP-4 transcripts are detected in chick epidermal ectoderm (not shown). lane 2: chick ventral neural plate explants (v) express only very low levels of BMP-4 mRNA when grown in vitro for 18 h. lane 3: rat epidermal ectoderm tissue induces high level BMP-4 expression when grown in contact with chick ventral neural plate explants. lane 4: recombinant BMP-4 induces BMP-4 expression in chick ventral neural plate explants. lane 5: recombinant BMP-7 induces BMP-4 expression in chick ventral neural plate explants. In all lanes, the amplified BMP-4 product is in the upper lane and S17 transcript in the lower lane. Similar results were obtained in at least three experiments.

FIGS. 10A–P. Identification of Dorsal Commissural Interneurons by Expression of LH-2 mRNAs and Protein. Panels A–E show the localization of LH-2 e mRNA as determined by non-isotopic in situ hybridization, and E–H show the localization of LH-2 proteins as determined by immunocytochemistry.

A–D: LH-2B mRNA (A) and protein (E) are first expressed at stages 19–20 by a small group of cells in the extreme dorsal region of the spinal cord, adjacent to the roof plate. B, R: At stage 22, the number of cells that express LH-2B mRNA (B) and LH-2 protein (F) has increased, and these cells are still dorsally located, adjacent to the roof plate.

C, G: At stage 24, cells express B mRNA and LH-2 proteins (G) are now detected both dorsally and in a more lateral and ventral position within the dorsal spinal cord.

D, H: At stage 27, some cells that express LH-2B mRNA (D) and LH-2 proteins (H) are located dorsally but the majority are located throughout the lateral region of the dorsal spinal cord. A large group of cells is present midway along the dorsoventral axis of the spinal cord, in the region that will give rise to deep dorsal horn laminae. Panels I–P show confocal images obtained using rabbit anti-LH-2 antibodies and monoclonal antibodies to other LIM homeodomain proteins or other markers.

I. Coexpression of LH-2 (green) and the neuronal cytoplasmic antigen Cyn-1 (red) shows the LH-2$^+$ cells are neurons.

J. Lack of coexpression of LH-2 (red) and msx-1/msx-2 proteins (green). msx-1/msx-2 proteins are restricted to dividing progenitor cells in the dorsal neural tube. Note that msx-1/msx-2 expression in the dorsal ventricular zone adjacent to LH-2$^+$ neurons is more intense than in more ventral regions.

K, L. LH-2 expression (red) defines a population of dorsal interneurons distinct from those that express Lim-1/Lim-2 at stage 22 (K) and 26 (L). Coexpression of these LIM homeodomain proteins is not detected at any developmental stage.

M, N. LH-2 expression (red) defines a population of dorsal interneurons distinct from those that express Isl-1 (green) at both stages 22 (M) and 26 (N). Note that Isl-1$^+$ interneurons are always located ventral and medial to LH-2$^+$ interneurons.

O. Section through stage 25 spinal cord showing that LH-2$^+$ interneurons (red) coexpress the surface glycoprotein TAG-1/Axonin-1 (green). The most dorsal LH-2$^+$ interneurons at this stage do not express TAG-1, suggesting that LH-2 proteins appear before TAG-1 in the differentiation of this neuronal subset. Note that many ventral TAG-1$^+$ cells do not express LH-2. LH-2$^+$ interneurons in rat also coexpress TAG-1 (not shown).

P. Section through stage 25 spinal cord showing that dorsal Isl-1$^+$ interneurons (green) do not coexpress TAG-1 (red).

Scale bar=um.

FIGS. 11A–H. Differentiation of LH-2$^+$ Interneurons In Vivo in Response to Dorsal Notochord Grafts and Notochord Removal.

A. Position of LH-2$^+$ interneurons in dorsal spinal cord neurons in a stage 24 chick embryo at a level two segments away from the region of a dorsal notochord graft.

B. Sections through the same embryos shown in (A) at a segmental level at which a dorsal notochord graft (n') is present. No LH-2$^+$ interneurons are detected in the dorsal spinal cord.

C. Section adjacent to that shown in (A) showing expression of Islet-1 in motor neurons ventrally and in dorsal interneurons close to LH-2$^+$ interneurons.

D. Section adjacent to that in (B), showing the continuous presence of Isl-1$^+$ neurons along the dorsoventral extent of the spinal cord after a dorsal notochord graft. It is unclear whether the dorsal Isl-1$^+$ neurons represent ectopic motor neurons or interneurons.

E. Expression of LH-2 in dorsal neurons in the spinal cord of a stage 25 embryo two segments away from the level at which the notochord has been removed. A notochord is present at this level.

F. Section from the same embryo as that in (E) showing the persistence of LH-2$^+$ interneurons at levels lacking a notochord. Note that the position of LH-2$^+$ interneurons is similar to that at levels at which the notochord is present.

G. Expression of Isl-1 in motor neurons and dorsal interneurons in a section serial to that shown in (E). A notochord is present at this level.

H. Section serial to that in (F) showing the absence of Isl-1$^+$ neurons in the ventral region of the spinal cord at levels lacking a notochord. Isl-1$^+$ neurons persist in the dorsal half of the spinal cord and their position along the dorsoventral axis is similar to that observed at levels of the same embryo in which the notochord is present (G).

I. Expression of the floor plate marker FP1 in a section through the spinal cord of a stage 25 embryo two segments away from the level at which the notochord has been removed. A notochord is present at this level (not shown).

J. FP1 is not expressed in the spinal cord of the same embryo shown in (I) at a level at which the notochord had been removed 72 h earlier. Note the characteristic change in morphology of the ventral spinal cord and the absence of wedged floor plate cells.

Scale bar=um.

FIGS. 12A–L. LIM Homeodomain Protein Expression Defines the Differentiation of Distinct Neuronal Populations in Neural Plate Explants.

A–C. LH-2$^+$ neurons differentiate in dorsal (d) but not intermediate (i) or ventral (v) neural plate explants grown in vitro for 48–72 h.

D–F. Isl-1$^+$ neurons differentiate in dorsal and ventral but not in intermediate neural plate explants grown in vitro for 48–72 h.

G–I. Isl-2$^+$ neurons differentiate in ventral but not intermediate or dorsal neural plate explants grown in vitro for 48–72 h.

J–L. Lim-1$^+$/Lim-2$^+$ neurons differentiate in dorsal, intermediate and ventral neural plate explants grown in vitro for 48–72 h.

Scale bar=um.

Figure 13A:
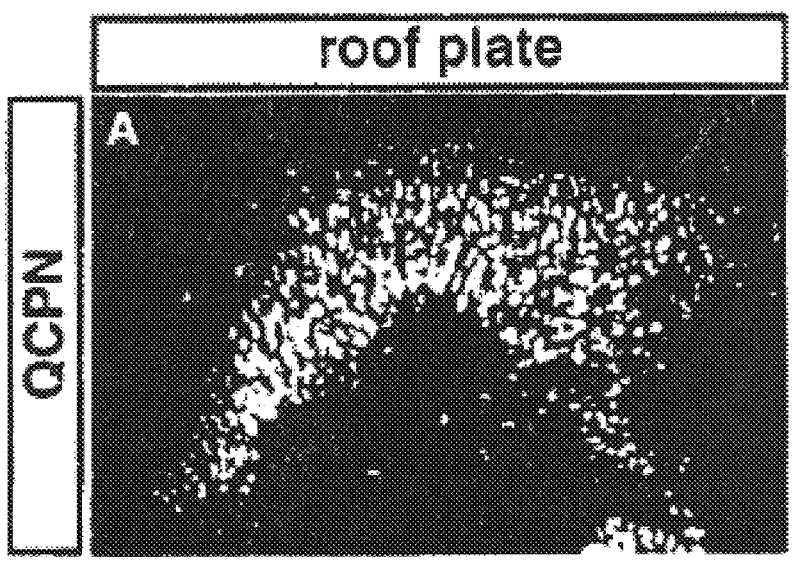
Figure 13B:
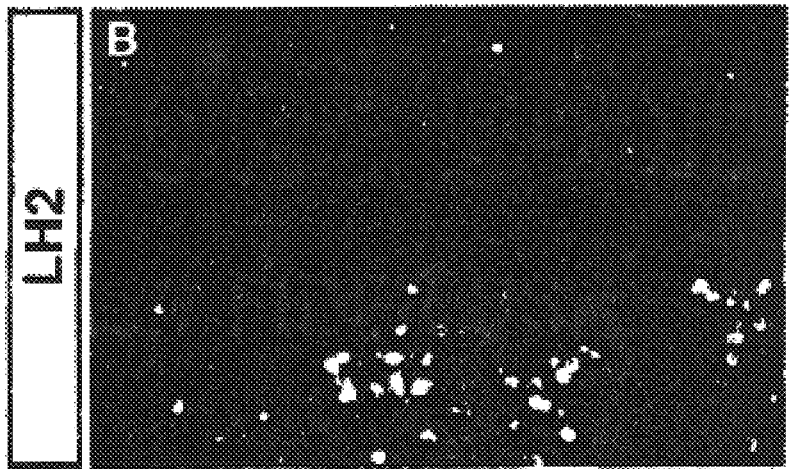
Figure 13C:
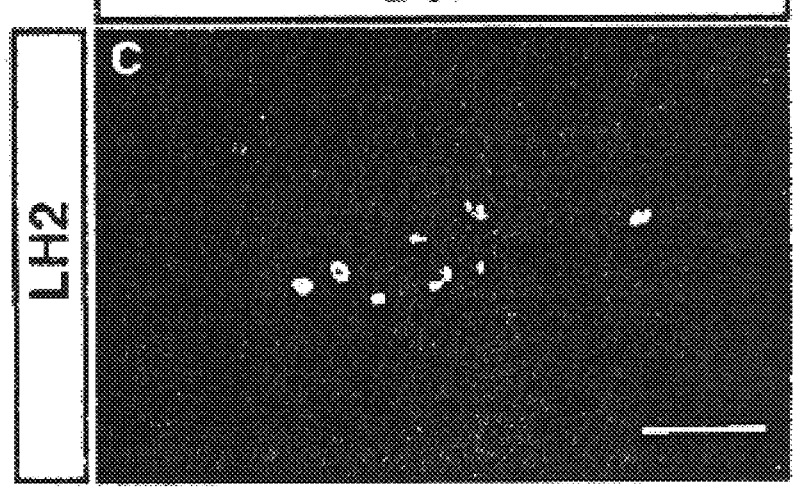
Figures 14A, 14B, 14C:
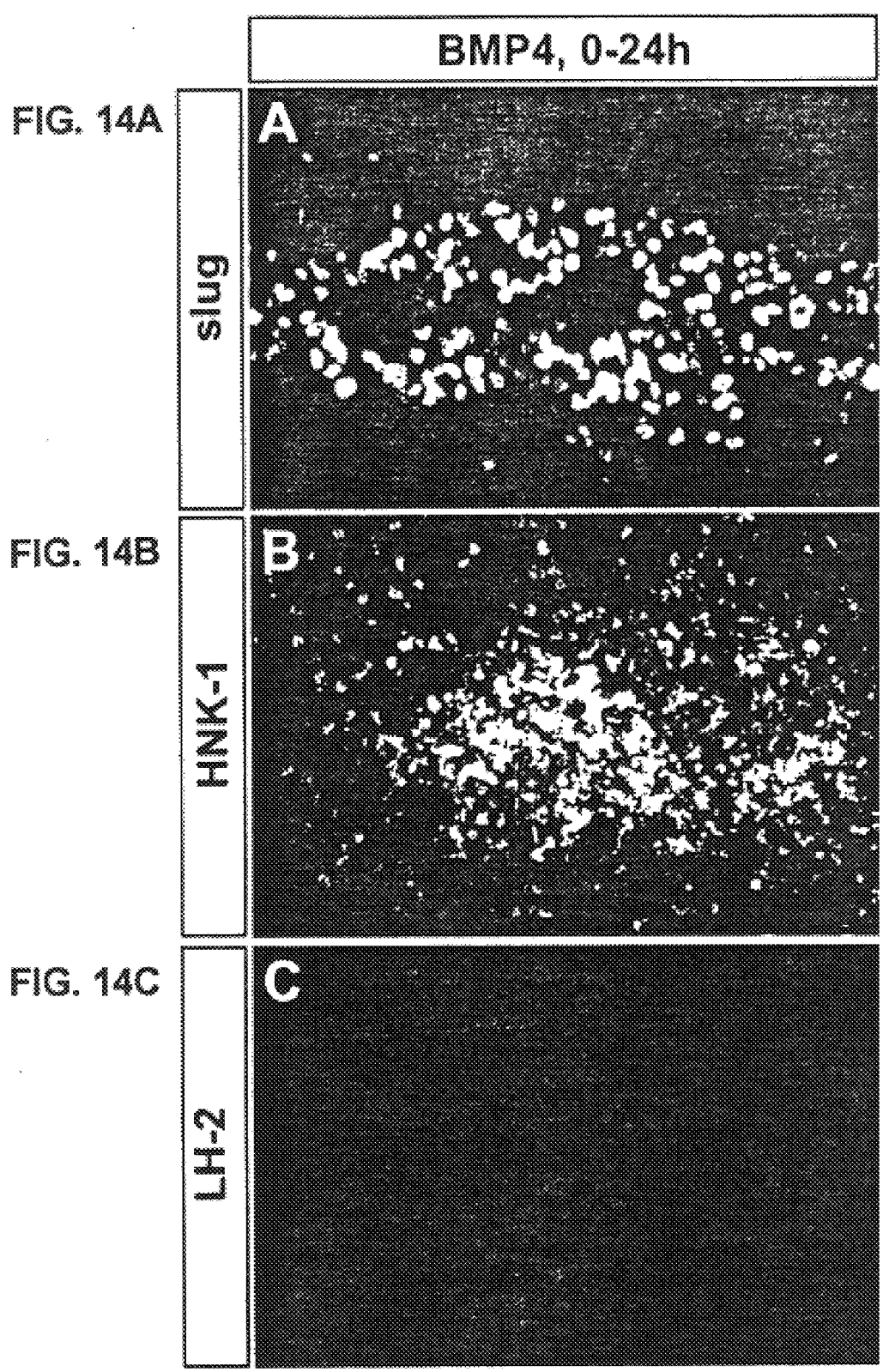
Figure 14D:
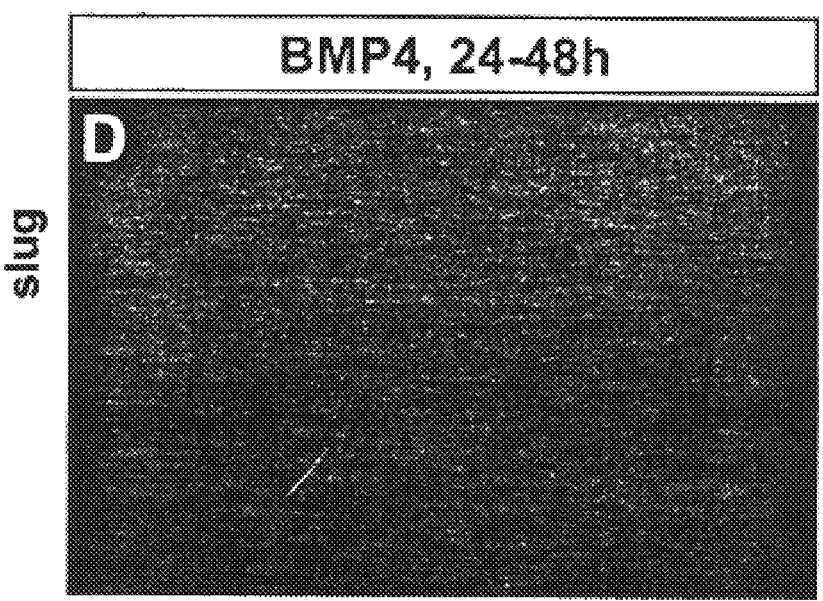
Figure 14E:
Figure 14F:
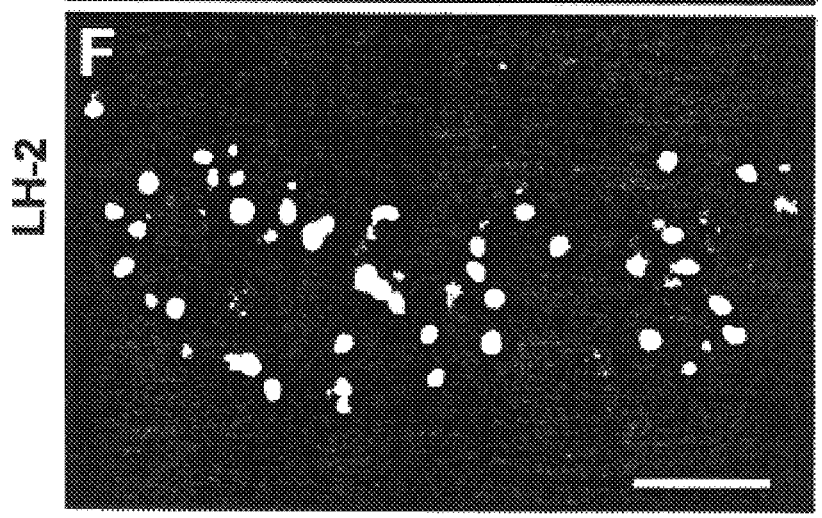

FIGS. 13A–C. Induction of LH-2$^+$ Interneurons in Neural Plate Explants by Roof Plate Cell and BMPs.

A. Intermediate (i) neural plate explants grown alone in vitro for 72 h do not generate LH-2$^+$ interneurons.

B. LH-2$^+$ interneurons (green) are induced in chick intermediate neural plate explants by stage 20 quail roof plate tissue. Quail cells are identified by expression of QCPN antigen (red). Note that some LH-2$^+$ interneurons differentiate in quail tissue, suggesting that the quail explant contains tissue lateral to the roof plate.

C. LH-2$^+$ interneurons (green) are induced in chick intermediate neural plate explants by stage 24 quail roof plate tissue. Note that few LH-2$^+$ interneurons differentiate in the quail (QCPN$^+$, red) inducing tissue.

D. Induction of LH-2$^+$ interneurons in intermediate neural plate explants exposed to recombinant BMP-4.

E. Induction of LH-2$^+$ interneurons in intermediate neural plate explants exposed to recombinant BMP-7 for 48 h.

F. Induction of LH-2$^+$ interneurons in intermediate neural plate explants exposed to recombinant Dsl-1 for 48 h.

Scale bar=um.

FIGS. 14A–F. A Temporal Switch in the Developmental Potential of Neural Plate Cells Exposed to BMP-4.

A–C. Intermediate neural plate explants isolated from stage 10 caudal neural plate generate slug$^+$ premigratory neural crest cells (A) and HNK-1$^+$ migratory neural crest cells (B) but not LH-2$^+$ interneurons when exposed to BMP-4 for a 24 h period, starting at the time of initial culture.

D–F. Equivalent intermediate neural plate explants grown in vitro for 24 h in the absence of exogenous BMP followed by exposure of BMP-4 for a subsequent 24 h period do not generate slug$^+$ premigratory neural crest cells (D), HNK-1$^+$ migratory neural crest cells (E) but do generate LH-2$^+$ interneurons (F).

Scale bar=um.

DETAILED DESCRIPTION OF THE INVENTION

This invention provides a composition for stimulating neural crest cell differentiation comprising an amount of a purified protein selected from a group consisting of bone morphogenetic protein 4, bone morphogenetic protein 5, bone morphogenetic protein 7, dorsalin-1 and combinations thereof effective to stimulate neural crest cell differentiation and an acceptable carrier. In an embodiment, the composition is used in a subject. In a further embodiment, the subject is a patient.

This invention also provides methods for stimulating neural crest cell differentiation in a culture comprising administering the above composition to the culture.

This invention provides a method for stimulating neural crest cell differentiation in a subject comprising administering to the subject the above composition.

This invention provides a composition for regenerating nerve cells in a subject comprising an amount of a purified protein selected from a group consisting of bone morphogenetic protein 4, bone morphogenetic protein 5, bone morphogenetic protein 7, dorsalin-1 and combinations thereof effective to regenerate nerve cells and an acceptable carrier. In an embodiment, the composition is used in cells. The cells may be cultured cells.

As used herein, "acceptable carriers" means any of the standard acceptable carriers. Examples include, but are not limited to, phosphate buffered saline, physiological saline, water and emulsions, such as oil/water emulsions.

This invention provides a method for regenerating nerve cells in a subject comprising administering to the subject the above composition.

This invention also provides a composition for promoting bone growth comprising an amount of the purified protein selected from a group consisting of bone morphogenetic protein 4, bone morphogenetic protein 5, bone morphogenetic protein 7, dorsalin-1 and combinations thereof effective to promote bone growth and an acceptable carrier. This invention also provides a composition for promoting bone growth in a subject comprising an amount of the purified protein selected from a group consisting of bone morphogenetic protein 4, bone morphogenetic protein 5, bone morphogenetic protein 7, dorsalin-1 and combinations thereof effective to promote bone growth and an acceptable carrier. This invention further provides methods for promoting bone growth in a subject comprising administering to the subject the above composition. In an embodiment, the composition is used in cells. The cells may be cultured cells.

This invention provides a composition for promoting wound healing comprising an amount of the purified protein selected from a group consisting of bone morphogenetic protein 4, bone morphogenetic protein 5, bone morphogenetic protein 7, dorsalin-1 and combinations thereof effective to promote wound healing and an acceptable carrier. This invention provides a composition for promoting wound healing in a subject comprising an amount of the purified protein selected from a group consisting of bone morphogenetic protein 4, bone morphogenetic protein 5, bone morphogenetic protein 7, dorsalin-1 and combinations thereof effective to promote wound healing and an acceptable carrier. This invention also provides methods for promoting wound healing in a subject comprising administering to the subject the above composition.

This invention provides a composition for treating neural tumor in a subject comprising an amount of the purified protein selected from a group consisting of bone morphogenetic protein 4, bone morphogenetic protein 5, bone morphogenetic protein 7, dorsalin-1 and combinations thereof effective to inhibit neural tumor cell growth and an acceptable carrier. In an embodiment, the neural tumor is neurofibroma. In another embodiment, the neural tumor is Schwann cell tumor.

This invention also provides methods for treating neural tumor in a subject comprising administering to the subject the above composition. In an embodiment, the neural tumor is neurofibroma. In another embodiment, the neural tumor is Schwann cell tumor.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Experimental Procedures cDNA Clones

Pax-3 (Goulding et al., 1993), msx-2 (Takahashi et al., 1992; Yokouchi et al., 1991), slug (Nieto et al., 1994) and s17 (Trueb et al., 1988) sequences were isolated by RT-PCR. BMP-2, BMP-4, BMP-5, BMP-6 and BMP-7 sequences were isolated by RT-PCR using degenerate primers (Basler et al., 1993). PCR fragments were used to isolate cDNA clones encoding BMP-4, BMP-5, and BMP-7. Chick BMP-2 and BMP-4 cDNAs were provided by P. Brickell (Francis et al., 1994), a BMP-6 cDNA by C. Hume and a pax-3 cDNA by M. Goulding. A BMP-4 cDNA was provided by R. Derynck and a human BMP-7 cDNA by M. Jones and A. Furley.

Antibodies

MAb 4 G1 recognizes msx-1 and msx-2. Slug protein was detected with a mouse serum antibody. Mab QCPN (Developmental Studies Hybridoma Bank) detects quail perinuclear antigens, Mab Not-1 (Yamada et al., 1991) detects notochord. MAb HNK-1 identifies migrating neural crest cells (Tucker et al., 1984).

Immunocytochemistry

Immunocytochemical detection of antigens in tissue sections and neural plate explants was performed as described (Yamada et al., 1993).

In Situ Hybridization

Whole-mount in situ hybridization was performed with digoxigenin-labeled probes essentially as described (Ericson et al., 1995).

Competitive PCR Analysis

PCR analysis was performed as described (Tanabe et al., 1995). Details are available on request.

COS Cell Transfections

COS cells were transfected using Lipofectamine (Gibco BRL) (Roelink et al. 1994) with BMP-4 (in pMT 21), BMP-7 (in pcDNA) or Dsl-1 (in pMT 21). Expression constructs encoding the full length SHH protein (Roelink et al., 1994) or its amino terminal cleavage product (Porter et al., 1995) were transfected into COS cells (Roelink et al., 1994, 1995).

Neural Plate Assays

Notochord and ventral, intermediate or dorsal neural plate explants were dissected from the caudal region of stage 10 (Hamburger and Hamilton, 1951) chick embryos (Yamada et al., 1993). Epidermal ectoderm tissue was dissected from an area lateral to the neural plate at caudal levels of stage 10 chick embryos, unsegmented paraxial mesoderm from a region caudal to the first somite. Conjugates formed between notochord, epidermal ectoderm or paraxial mesoderm and neural plate were cultured essentially as described (Yamada et al., 1993).

Experimental Results

Molecular Markers of Dorsal Cell Differentiation

Applicants determined how dorsal fates are acquired by neural plate cells by analyzing the expression in situ and then in vitro of four genes expressed by cells in the dorsal half of the neural tube: msx-1, pax-3, Dsl-1 and slug.

Applicants examined the pattern of neural expression of pax-3 and msx-1 at caudal levels of stage 10 chick embryos. In the newly-formed neural plate, cells at all mediolateral positions expressed pax-3 mRNA, msx-1 mRNA and msx-1/2 proteins (termed msx) (FIGS. 1A, E, I). At more rostral levels at which the neural plate has begun to fold, pax-3 and msx were not expressed medially (FIGS. 1B, F, J). At a level just caudal to the point of neural tube closure, the expression of pax-3 and msx was restricted to the most lateral, prospective dorsal, region of the neural folds (FIGS. 1C, G, K). Consistent with previous observations (Goulding et al., 1993; Robert et al., 1991; Takahashi et al., 1992), pax-3 and msx were restricted to dorsal regions of the closed neural tube (FIGS. 1D, H, L). Thus, the expression of pax-3 and msx appears to delineate an early stage in the differentiation of neural plate cells, irrespective of their eventual dorsoventral fate.

The early extinction in expression of these two genes from the midline of the neural plate suggests that signals from the notochord are responsible for their repression. In support of this, notochord grafts repress the dorsal expression pax-3 in the neural tube in vivo (Goulding et al., 1993) and repress pax-3 and msx expression in vitro (see below). Conversely, notochord removal results in expression of pax-3 in the ventral neural tube (Goulding et al, 1993). Thus, the expression of pax-3 and msx by dorsal neural tube cells appears to be acquired by default, in the sense that these genes are initially expressed uniformly within the neural plate and are subsequently repressed from prospective ventral regions by notochord-derived signals.

In contrast to pax-3 and msx, Dsl-1 expression was not detected in neural plate cells (FIG. 2A), appearing dorsally only after neural tube closure (Basler et al., 1993). Thus, Dsl-1 expression is associated with the differentiation of cells in the dorsal neural tube but does not appear to define a specific dorsal cell type.

The slug protein was not expressed by early neural plate cells (FIG. 1M, Nieto et al., 1994) and appears in cells in the extreme lateral region of the neural plate only after it has begun to fold (FIGS. 1N, O). After neural tube closure, slug$^+$ cells were found at the most dorsal extreme of the neural tube (FIG. 1P) and define a single dorsal cell type, premigratory neural crest cells (Nieto et al, 1994).

Dorsal Fates of Neural Plate Cells Grown In Vitro

With these four genes as markers, applicants examined the differentiation of cells in explants derived from prospective ventral, intermediate and dorsal regions of the neural plate isolated from the caudal region of stage 10 chick embryos (a level similar to that shown in FIGS. 1B, F, J).

Ventral neural plate explants examined at the time of isolation (data not shown) and after 18 h in culture expressed few, if any, msx$^+$ cells (FIG. 3A) but did express low levels of pax-3 (FIG. 2A). The absence of expression of msx suggested that cells in ventral neural plate explants have been exposed to a notochord-derived signal at the time of isolation. Consistent with this, cells in ventral neural plate explants give rise to motor neurons when grown alone in vitro (Yamada et al., 1993). Although ventral neural plate explants appear to have been exposed to notochord-derived signals, Dsl-1 expression was detected at low levels in these explants after 18 h in vitro (FIG. 2A). This finding, together with the ventral expression of Dsl-1 after elimination of the notochord (Basler et al., 1993) suggests that the continued presence of notochord-derived signals is necessary to repress Dsl expression in prospective ventral regions of the neural tube. Thus, Dsl-1 may also achieve its dorsally-restricted expression in the neural tube through inhibition of its expression ventrally. No slug$^+$ cells were detected in ventral neural plate explants (FIG. 3D) and after 40 h migratory neural crest cells, as defined by HNK-1$^+$ expression were not detected (FIG. 3G). Thus, cells in ventral neural plate explants that have been exposed to notochord-derived signals do not give rise to definitive dorsal cell types.

In intermediate neural plate explants examined at the time of isolation (data not shown) and after 18 h, virtually all cells expressed msx (FIG. 3B). Pax-3 expression was also detected (FIG. 2A). The detection of msx suggests that cells in intermediate neural plate explants have not been exposed to notochord-derived signals at the time of isolation. To examine whether msx expression does indeed provide a sensitive indicator of the exposure of neural plate cells to notochord-derived signals, intermediate neural plate explants were grown for 18 h in contact with notochord. The expression of msx by neural cells was repressed over a distance of >100 (m from the junction of the explants (FIG. 3J and data not shown). Msx expression was also repressed when neural plate explants were grown transfilter to a notochord explant (data not shown), providing evidence that the repressive effect of the notochord is mediated by a diffusible factor. Applicants tested whether SHH mimics the notochord-derived factor by growing intermediate neural plate explants on COS cells transfected with Shh. Msx expression was repressed under these conditions (FIGS. 3K, L), suggesting that SHH mediates the long-range notochord-derived repression of msx detected in vitro and inferred in viva. The detection of msx in intermediate neural plate explants therefore supports the idea that cells in these explants have not been exposed to notochord-derived signals at the time of isolation.

Although Dsl-1 was not detected in intermediate neural plate explants at the time of their isolation, the gene was expressed after 18 h in vitro (FIG. 2A). More informatively, intermediate neural plate explants did not contain slug$^+$ cells or give rise to migratory HNK-1$^+$ cells (FIGS. 3E, H). Similarly, the differentiation of a subset of dorsal commissural neurons defined by expression of the LIM homeodomain protein LH-2 did not occur (Tremml et al., in preparation). These results provide evidence that definitive dorsal cell types do not differentiate simply as a consequence of isolating neural plate cells from the influence of notochord-derived signals.

Dorsal neural plate explants examined after 18 h in culture contained msx$^+$ cells, (FIG. 3C) and expressed high levels of pax-3 and Dsl-1 (FIG. 2A). These explants, however, did contain slug$^+$ cells (FIG. 3F) and gave rise to migratory HNK-1$^+$ cells (FIG. 3I), suggesting that cells in dorsal neural plate explants have been exposed to dorsalizing signals at the time of their isolation.

Taken together, this analysis of cell differentiation in neural plate explants suggests that certain genes characteristic of dorsal neural tube cells (pax-3, msx) are acquired by default but that the acquisition of distinct dorsal cell fates requires additional inductive signals.

Epidermal Ectoderm is the Source of a Dorsalizing Signal

To define the source of dorsalizing signals, applicants examined whether the dorsal differentiation of neural plate cells could be induced by tissues adjacent to the neural plate. Applicants focused on epidermal ectoderm and paraxial mesoderm since these tissues have been implicated in the differentiation of neural crest cells. Ventral neural plate explants were grown in contact with epidermal ectoderm or paraxial mesoderm derived from stage 10 quail or chick embryos and assayed for the expression of slug and HNK-1$^+$ migratory cells. In addition, applicants assayed expression of msx (and Dsl-1 and pax-3) to determine if inductive signals could also overcome an earlier repressive influence of the notochord.

Figure 2B:
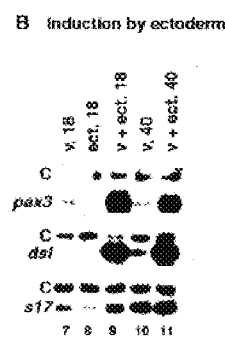

Ventral or intermediate neural plate explants grown for 18 h in contact with epidermal ectoderm contained numerous slug$^+$ cells (FIGS. 4C, D and data not shown) and by 40 h, many HNK-1$^+$ neural crest cells had migrated from the explants (FIGS. 4G, J). Msx$^+$ cells were detected in the region of the explant closest to the ectoderm (FIGS. 4A, B) and high levels of pax-3 and Dsl-1 were also induced (FIG. 2B). In contrast, the induction of dorsal markers was not detected when neural plate explants were grown at a distance from epidermal ectoderm (data not shown). Moreover, no induction of dorsal markers was obtained in ventral neural plate explants grown in contact with paraxial mesoderm (data not shown). These results show that the epidermal ectoderm is the source of a contact-dependent signal that can induce the differentiation of neural crest cells in vitro, consistent with other studies (Dickinson et al., 1995; Selleck and Bronner-Fraser, 1995). They also show that epidermal ectoderm can overcome an earlier repressive influence of the notochord.

BMPs as Mediators of Epidermal Ectoderm-Derived Signals.

The ability of epidermal ectoderm to induce dorsal cell differentiation in ventral neural plate explants served as the basis of an assay to identify ectodermally-derived factors that dorsalize ventral neural plate cells. Although not expressed in the epidermal ectoderm, Dsl-1 induces neural crest cells (Basler et al., 1993). Applicants therefore examined whether members of the TGFβ family that are related structurally to Dsl-1 are expressed in the epidermal ectoderm at the time that dorsalization of the neural plate is thought to occur.

Degenerate PCR primers were used to isolate Dsl-1-related genes expressed in the region of the epidermal ectoderm that flanks the neural plate in stage 10 chick embryos. Of thirteen PCR products cloned, three encoded BMP-4 (Francis et al., 1994), one BMP-5 (Kingsley, 1994) and nine BMP-7 (Houston et al., 1994). cDNAs encoding chick BMP-4, BMP-5 and BMP-7 were then used to determine the patterns of expression of these genes in stage 10 chick embryos. Applicants also analyzed the expression of BMP-2 and BMP-6 although these genes were not detected in the epidermal ectoderm by RT-PCR.

Figure 5E:
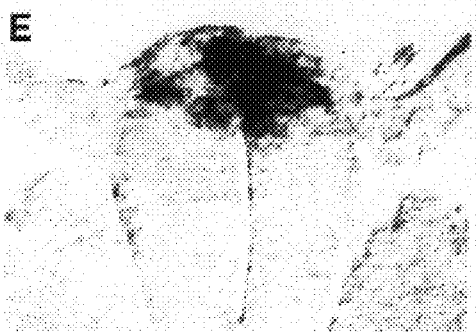
Figure 5F:
Figure 5G:
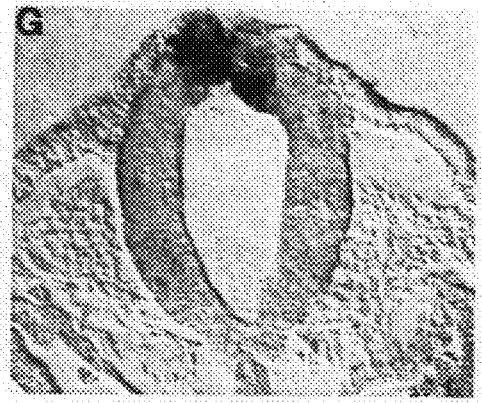
Figure 5H:
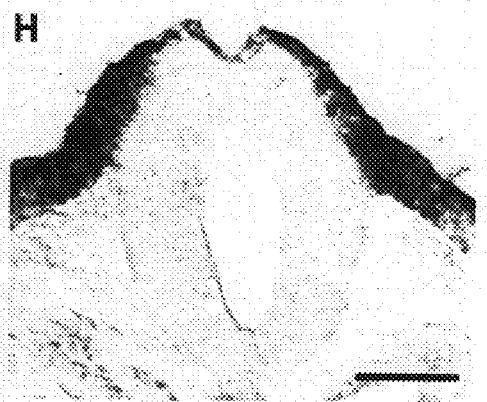

Epidermal ectodermal cells flanking the caudal neural plate expressed both BMP-4 and BMP-7 but not BMP-2, BMP-5 or BMP-6 (FIGS. 5A, B and data not shown). BMP-4 and BMP-7 expression was lost from the epidermal ectoderm at the level of neural tube closure (FIGS. 5C–F) with the exception that BMP-4 expression persisted in ectodermal cells at the dorsal midline of the caudal neural tube (FIGS. 5C, E). At prospective midbrain and forebrain levels of the neural tube, BMP-7 expression was maintained at high levels in the epidermal ectoderm (FIG. 5H). BMP-4 was also expressed by cells in the dorsal folds of the neural plate and subsequently at high levels by cells at the dorsal midline of the neural tube (FIGS. 5C, E, G). BMP-7 was also expressed, albeit at much lower levels by cells in the dorsal region of the caudal neural tube (FIG. 3F and data not shown).

The pattern of expression of BMP-4 and BMP-7 raised the possibility that these two proteins mediate the ability of the epidermal ectoderm to initiate dorsal cell differentiation in neural plate cells. To test this, cDNA-derived expression vectors encoding BMP-4 and BMP-7 were transfected into COS cells. Medium from BMP-4- or BMP-7-transfected COS cells enhanced the expression of pax-3 and Dsl-1 and induced msx$^+$ cells, slug$^+$ cells and migratory HNK-1$^+$ cells in ventral neural plate explants (FIGS. 2C, 6D–I). Medium derived from untransfected COS cells or cells that had been transfected with a truncated Dsl-1 cDNA did not induce any of these markers (FIG. 2C; FIGS. 6A–C). Thus, BMP-4 and BMP-7 mimic the ability of epidermal ectoderm to induce or elevate the expression of markers of dorsal neural tube cells and to promote the differentiation of neural crest cells.

Figure 2C:
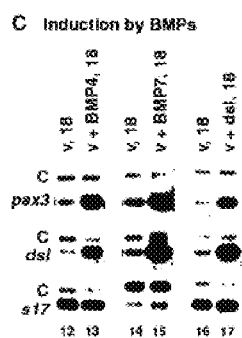

The expression of BMP-4, BMP-7 and Dsl-1 by cells in the dorsal region of the neural tube and the induction of Dsl-1 expression by epidermal ectoderm raised the possibility that neurally-expressed BMPs are induced by BMP-mediated signals from the epidermal ectoderm. To test this, applicants examined whether Dsl-1 is induced in ventral neural plate explants by BMP-4 or BMP-7. Explants exposed to BMP-4 or BMP-7 were induced to express high levels of Dsl-1 (FIG. 2C). Moreover, Dsl-1 ($3 \times 10^{-11}$ M) mimicked the ability of BMP-4 and BMP-7 to enhance pax-3 and Dsl-1 expression and to induce $msx^+$ cells, $slug^+$ cells and the emigration of $HNK-1^+$ cells in ventral neural plate explants (FIGS. 2C; FIG. 6 lane J–L). Thus, BMPs expressed by dorsal neural cells appear to provide a secondary source of dorsalizing signals that might operate at a time when the epidermal ectoderm is no longer in contact with the neural epithelium.

Opponent Actions of Dorsalizing and Ventralizing Signals

Figure 2D:

The long-range repression of msx expression detected in vitro and inferred in vivo suggests that a ventralizing signal from the notochord might normally block the spread of BMP-mediated dorsalizing signals within the neural tube. Applicants therefore examined whether the acquisition of dorsal cell fates in dorsal neural plate explants could be repressed by the notochord. Dorsal neural plate explants grown in contact with notochord expressed few, if any, $msx^+$ cells (FIG. 7A) and exhibited markedly reduced levels of pax-3 and Dsl-1 (FIG. 2D). In addition, the number of $slug^+$ cells was reduced by 90% (FIG. 7B) and the number of migratory $HNK-1^+$ cells was reduced by 80% (FIG. 7C). Similarly, exposure of dorsal neural plate explants to SHH almost completely eliminated msx, pax-3 and Dsl-1 expression (FIGS. 2D, 7D), reduced by 96% the number of $slug^+$ cells (FIG. 7E) and by 72% the number of migratory $HNK-1^+$ cells (FIG. 7F). Although some neural crest cells were detected in the presence of ventralizing signals (see also Artinger and Bronner-Fraser, 1992) these results show that the majority of cells in lateral regions of the neural plate are not committed to dorsal fates prior to neural tube closure. The repression of an ongoing program of dorsal cell differentiation by a SHH-mediated signal from the notochord supports the idea that, in vivo, an equivalent activity normally restricts the domain of dorsal cell differentiation within the neural tube.

The progressive spread of this long-range ventralizing signal from the notochord could eventually influence the entire neural plate. The expression of dorsal cell properties in lateral regions of the neural plate might therefore result from the ability of signals from the epidermal ectoderm to maintain dorsal markers in cells that are exposed to notochord-derived signals. To address this issue, dorsal neural plate explants were grown in vitro, flanked on one side by notochord and on the other by epidermal ectoderm. The number of $slug^+$ cells and migratory $HNK-1^+$ cells detected in explants grown with the notochord and epidermal ectoderm was ~4-fold greater than that found in explants grown in contact with the notochord alone (FIGS. 7H–I). Moreover, virtually all $slug^+$ cells were located close to the ectoderm. The epidermal ectoderm was also able to maintain msx expression locally in neural plate explants grown in contact with the notochord (FIG. 7G). Signals from the epidermal ectoderm may, therefore, normally ensure dorsal cell differentiation by counteracting, locally, a long-range ventralizing influence of the notochord.

Finally, applicants tested whether the ability of the epidermal ectoderm to maintain dorsal cell fates in the presence of ventralizing signals from the notochord is mimicked by BMPs. Ventral neural plate explants grown in contact with the notochord but in the presence of BMP-4 contained $msx^+$ cells, $slug^+$ cells and migratory $HNK-1^+$ cells (FIGS. 7J–L and data not shown) and exhibited elevated levels of pax-3 and Dsl-1 (data not shown). Under these conditions, the expression of slug and msx was largely restricted to neural plate cells located at a distance of >~50 (m from the notochord (FIGS. 7J, K) suggesting that in the vicinity of the notochord, cell fate is still dominated by ventralizing signals. These results suggest that BMPs mediate the ability of the epidermal ectoderm to maintain dorsal cell fates in the presence of notochord-derived signals.

Experimental Discussion

These studies have examined the cellular interactions that control the differentiation of cell types generated in the dorsal region of the neural tube. Applicants' results provide evidence that neural plate cells acquire dorsal cell fates in part through the maintenance of genes expressed throughout the neural plate at earlier stages and in part as a response to localized inductive signals. They also establish three points about the origin and nature of these signals. First, the epidermal ectoderm that flanks the lateral border of the neural plate represents a source of signals that dorsalizes neural plate cells. Second, the TGFβ-like molecules BMP-4 and BMP-7 are expressed in the epidermal ectoderm and both proteins mimic its dorsalizing activity. Third, BMP-mediated signals from the epidermal ectoderm can ensure the differentiation of dorsal cell types by opposing the actions of a long-range SHH-mediated ventralizing signal from the notochord. These findings suggest that acquisition of dorsal cell properties by neural plate cells is dependent on the opponent activities of BMPs from the epidermal ectoderm and SHH from the notochord.

The notochord has also been implicated in the ventralization of paraxial mesoderm (Pourquie et al. 1993, Brand-Saberi et al., 1993; Fan and Tessier-Lavigne, 1994) through an activity that appears to be mediated by SHH (Johnson et al., 1994; Fan and Tessier-Lavigne, 1994; Fan et al., 1995). Moreover, the epidermal ectoderm is the source of an as yet unidentified signal that dorsalizes the paraxial mesoderm (Fan and Tessier-Lavigne, 1994). Thus, the establishment of dorsoventral pattern within the neural plate and paraxial mesoderm appears to be achieved through a common cellular strategy and at least in part, through the same inductive factors.

The Early Character of Neural Plate Cells.

The possibility that the acquisition of dorsal fates represents a default state in the differentiation of neural plate cells was raised by the observation that elimination of the notochord not only failed to inhibit the differentiation of dorsal cell types but also resulted in the expression of certain dorsal markers throughout the entire dorsoventral axis of the neural tube (Yamada et al., 1991; Goulding et al., 1993; Basler et al., 1993). The present in vitro assays provide evidence that cells in neural plate explants that have not been exposed to ventralizing signals do acquire several dorsal characteristics yet fail to differentiate into definitive dorsal cell types. Thus, definitive dorsal fates are not acquired by default.

Pax-3 and msx-1 are required for the differentiation of neural crest cells and their derivatives (Stuart et al., 1994; Satokata and Maas, 1994), but the present results suggest that expression of these two transcription factors is not sufficient to confer definitive dorsal identities upon neural plate cells. Similarly, applicants' studies show that even though Dsl-1 can induce dorsal cell types, its expression by cells in intermediate neural plate explants is insufficient to promote their differentiation. This might be because the level of Dsl-1 expressed is below the threshold for induction of dorsal cell types. In addition, the competence of neural plate cells to respond to inductive signals is lost rapidly (Yamada et al., 1991, 1993, Placzek et al. 1993; K. L., unpublished data), thus cells may have lost the competence to respond to Dsl-1 by the time that it is expressed.

BMPs as Dorsalizing Signals from the Epidermal Ectoderm

The present findings, taken together with other studies on neural crest cells (Moury and Jacobson, 1989, 1990; Dickinson et al., 1995; Selleck and Bronner-Fraser, 1995) provide evidence that the epidermal ectoderm is the source of signals that induce dorsal cell differentiation in lateral regions of the neural plate. The local action of these dorsalizing signals is supported by the early lateral restriction in expression of the dorsal markers slug (FIG. 1, Nieto et al., 1994), cadherin 6B (Nakagawa and Takeichi, 1995) and BMP-4 within the neural plate. The action of signals from the epidermal ectoderm might underly the rapid generation of neural crest cells in the ventral half of the neural tube that is observed after excision of dorsal neural tube at cranial levels (Scherson et al., 1993).

The route by which ectodermal signals are transmitted to lateral neural plate cells has not been resolved. The epidermal ectoderm and neural plate are initially contiguous, thus a dorsalizing signal could be transmitted through the plane of the epithelium. However, during the folding of the neural plate, the basal surface of the ectoderm contacts the lateral, prospective dorsal region of the neural plate (Martins-Green, 1988), providing an extended interface for the transmission of ectodermally-derived signals.

The major support for the idea that BMPs mediate the dorsal inductive activity of the epidermal ectoderm derives from two observations. First, two members of this family, BMP-4 and BMP-7, are expressed in the surface ectoderm at the time that the neural plate is formed. BMP-4 and BMP-7 are also expressed in the surface ectoderm in other vertebrate embryos (Jones et al., 1991; Lyons et al., 1995; Fainsod et al., 1994). Second, BMP-4 and BMP-7 mimic the ability of the epidermal ectoderm to dorsalize neural plate cells. Additional TGFβ-like molecules could contribute to the inductive activity of the epidermal ectoderm. However, numerous other factors including EGF, FGFs neurotrophins and wnt-1 do not mimic the ability of BMPs to induce dorsal markers (K. L., H. R., unpublished observations). Thus, BMPs currently represent the sole candidates for mediators of ectodermally-derived dorsalizing signals. Nevertheless, the requirement for BMPs in the dorsalization of neural plate cells remains to be demonstrated.

Although the initial dorsalizing influence of the epidermal ectoderm appears to be a local event, BMP-4, Dsl-1 and low levels of BMP-7 appear to be induced in neural cells as a component of the program of dorsal cell differentiation. An initial short-range dorsalizing signal from the epidermal ectoderm is likely, therefore, to be propagated within the neural plate and neural tube through the actions of BMP-4, BMP-7, Dsl-1 and possibly other BMPS. This secondary source of BMPs may be important in promoting the differentiation of dorsal cell types that are generated at later times, after the epidermal ectoderm loses contact with the dorsal neural tube. The transfer of dorsalizing signals from the epidermal ectoderm to the dorsal midline of the neural tube is similar in principle to the strategy used to perpetuate ventralizing signals through their transfer from the notochord to the floor plate (Yamada et al., 1991; Placzek et al., 1993; Marti et al., 1995).

The present results, together with studies on dorsal commissural neurons (Tremml et al., unpublished data) suggest that BMP-mediated signals can induce many or all definitive dorsal cell types. Roof plate cells, neural crest cells and commissural neurons are generated at distinct positions in the dorsal half of the neural tube, raising the issue of whether the concentration of BMP to which a neural plate cell is exposed defines its specific fate. The expression of several BMPs in the epidermal ectoderm and in nested dorsal domains of the neural tube leaves open the additional possibility that the formation of BMP heterodimers confers qualitatively or quantitatively distinct inductive activities, through actions on subclasses of BMP receptors (Massague et al., 1994).

The response of neural cells to BMPs varies at different rostrocaudal levels of the neural tube. At spinal cord levels BMPs promote neural crest cell differentiation whereas in the hindbrain prospective neural crest cells in odd-numbered rhombomeres are induced to undergo apoptosis in response to BMP-4 (Graham et al., 1994). Thus, an early restriction in the rostrocaudal identity of neural plate cells appears to define the nature of their response to both dorsalizing and ventralizing (Ericson et al., 1995) inductive signals. Components of the response of neural cells to BMPs may, however, be conserved. Induction of msx gene expression is observed in response to BMP-4 at both spinal cord and at hindbrain levels (Graham et al., 1994). In addition, msx gene expression can be induced by BMP-4 in mesenchymal cells (Vainio et al., 1993).

Opponent Actions of BMPs and SHH

The present results, taken together with studies on ventral cell specification (see Smith, 1994; Johnson and Tabin, 1995), suggest that the patterning of the neural plate depends on the combined actions of a dorsalizing signal from the epidermal ectoderm and a ventralizing signal from the notochord. The ventralizing activity of SHH is likely to represent a major factor in confering the dorsal restriction in expression of msx, pax-3 and Dsl-1 and in limiting the domain of the neural tube within which the differentiation of definitive dorsal cell types can occur. It is possible, therefore, that the induction of ventral cell types by SHH requires the repression of genes such as msx-1 and pax-3. In addition, the maintenance of dorsal cell differentiation in lateral regions of the neural plate might depend upon the ability of ectodermally-derived BMPs to oppose a long-range SHH-mediated signal that spreads through the neural plate over time.

Although notochord-derived signals and SHH can suppress dorsal cell differentiation, Dsl-1 and BMP-4 can conversely, suppress the differentiation of ventral cell types (Basler et al., 1993). Thus, the fate of early neural plate cells is likely to depend on whether they are exposed to BMPs or to SHH, on the concentration of these factors and on the time of their exposure to them. In medial regions of the neural plate, SHH-mediated signals appear dominant whereas in lateral regions the influence of BMPs prevails. Cells that differentiate in the intermediate region of the neural plate exhibit distinct molecular properties (Rangini et al., 1991; Lu et al., 1992; Zimmerman et al., 1993). How such intermediate cell fates are established remains unclear.

Second Series of Experiments

Roof Plate-Dependent Patterning in the DorsalNeural Tube: Induction of Dorsal Commissural Interneurons by BMP-Mediated Signals During the early development of the vertebrate nervous system distinct cell types are generated at specific positions within the neural tube, establishing a primitive pattern that is later refined by cell migration and cell death. The generation and organization of cell types along the dorsoventral axis of the neural tube appears to depend initially on inductive signals that derive from non-neural tissues that lie adjacent to the neural plate: most notably axial mesodermal cells of the notochord and epidermal ectoderm cells. The generation of cell types that populate the ventral half of the neural tube; floor plate cells, motor neurons and ventral interneurons requires inductive signals from the notochord (Placzek, 1995). As a consequence, these ventral cell types fail to differentiate when the notochord is removed (Placzek, 1990; van Straaten, 1988; Yamada, 1991; Ericson, 1992). In addition, signals from the notochord can suppress the differentiation of dorsal cell types and induce the ectopic differentiation of floor plate cells and motor neurons when grafted adjacent to the dorsal neural tube (Placzek, 1990; van Straaten, 1988; Yamada, 1991; Ericson, 1992). These inductive activities of the notochord appear to be mediated by the Sonic Hedgehog (SHH) protein (Placzek, 1995 #322).

Progenitor cells in the dorsal half of the caudal neural tube give rise to three major cell types: roof plate cells at the dorsal midline, neural crest cells in and around the dorsal midline and sensory relay interneurons more laterally. The onset of differentiation of dorsal cell types is, however, not synchronous. For example, neural crest cell differentiation is initiated during the folding of the neural plate whereas dorsal sensory interneurons are generated considerably after neural tube closure. The differentiation of neural crest cells appears not to require a signal from the notochord since dorsal root ganglion neurons and Schwann cells, cell types derived from neural crest cells are formed after notochord removal (van Straaten and Hekking, 1991; Yamada et al., 1991). Instead, the differentiation of neural crest cells appears to depend on a contact-dependent inductive signal from cells of the epidermal ectoderm that flank the lateral borders of the neural plate (Moury, 1989; Dickinson, 1995; Selleck, 1995; Liem, 1995). This ectodermal inductive signal is mimicked by two members of the TGFα family, BMP-4 and BMP-7) (Basler, 1993; Liem, 1995) that are expressed in the epidermal ectoderm flanking the neural plate (Liem, 1995). Thus, BMPs are the most likely mediators of the neural crest inducing activity of the epidermal ectoderm. At the time of neural tube closure, however, the expression of BMP-4 and BMP-7 by the epidermal ectoderm ceases (Liem, 1995) and the epidermal ectoderm becomes separated from the dorsal neural tube. Thus, the source and identity of signals that induce cell types that remain within the dorsal neural tube, and in particular the sensory relay interneurons that are generated at later stages of neural development remains unclear.

In the ventral neural tube, each of the inductive activities initially exhibited by the notochord, and the expression of SHH, are subsequently acquired by floor plate cells at the ventral midline of the neural tube (Placzek, 1995). In previous studies, it was observed that BMP-4 and a related BMP, Dsl-1 are expressed by roof plate cells (Basler, 1993; Liem, 1995). This observation raised the possibility that dorsalizing inductive activities initially exhibited by the epidermal ectoderm might later be acquired by roof plate cells at the dorsal midline of the neural tube, in manner analagous to the transfer of ventralizing inductive signals from the axial mesoderm to the neural ectoderm. To test this possibility, the cellular origin and molecular identity of inductive signals required for the differentiation of two dorsal cell types: roof plate cells and a class of dorsal sensory interneurons that is generated close to the roof plate in the dorsal spinal cord was examined. The differentiation of roof plate cells, as with neural crest cells, appears to be induced at stages prior to neural tube closure by a BMP-mediated signal from the adjacent epidermal ectoderm. In contrast, a set of dorsal commissural interneurons which can be defined by expression of the LIM homeobox genes LH-2A and LH-2B, is generated well after neural tube closure and appears to be induced by a signal from the roof plate. This roof plate-derived inductive activity is mimicked by BMP-4, BMP-7 and Dsl-1, each of which is expressed by roof plate cells at the time that the first LH-2$^+$ interneurons differentiate.

These findings suggest that the roof plate and its resident BMPs have a critical role in the induction and patterning of specific classes of interneurons that are generated in the dorsal spinal cord. They also raise an additional issue: how are two distinct dorsal cell types, neural crest cells and dorsal sensory interneurons generated in response to the same inductive factors at markedly different times. The in vitro results suggest that the early onset of neural crest cell generation and the later onset of LH-2$^+$ interneuron generation is the result of a switch in the competence of neural plate cells to respond to BMPs.

Experimental Results

Induction of Roof Plate Differentiation by BMP-Mediated Signals from the Epidermal Ectoderm.

Figure 8A:
Figure 8B:
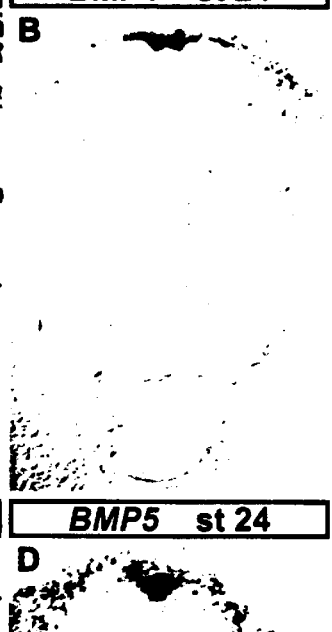
Figure 8C:
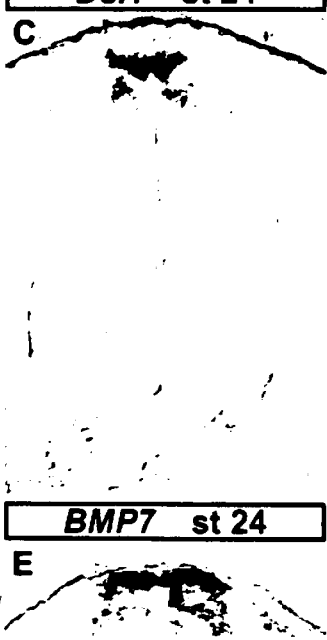
Figure 8D:
Figure 8E:
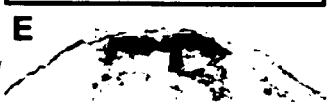
Figure 8F:

The differentiation of neural crest cells appears to be induced by a contact-dependent signal from the epidermal ectoderm that is mimicked by BMP-4 and BMP-7 (Liem, 1995). To examine the source of inductive signals involved in roof plate differentiation it was necessary to identify a definitive marker of roof plate cells. In previous studies it was found that BMP-4 is expressed in prospective roof plate cells soon after neural tube closure (Liem, 1995). It was therefore examined whether BMP-4 expression persists in and is selective for roof plate cells at later developmental stages. BMP-4 was expressed selectively by cells at the dorsal midline of the neural tube and later, spinal cord (FIGS. 8A, B, data not shown). Thus, BMP-4 expression provides a marker that can be used to asses the differentiation of roof plate cells.

To determine the timing, source and identity of signals that control roof plate differentiation, a RT-PCR assay was used to detect BMP-4 transcript expression in neural plate explants (Yamada, 1993). To provide information on the time of onset of roof plate differentiation BMP-4 expression was assayed in dorsal, intermediate and ventral regions of stage 10 caudal neural plate. At the time of isolation BMP-4 expression was detected in dorsal, but not intermediate or ventral explants (FIG. 9A) providing evidence that roof plate differentiation is underway in the prospective dorsal region of the neural folds, prior to neural tube closure. This results is consistent with previous studies showing BMP-4 expression in cells in the dorsal region of the neural folds in situ (Liem, 1995).

To determine whether signals from the epidermal ectoderm are responsible for initiating roof plate differentiation in neural plate cells, ventral neural plate explants were grown in vitro for 24 h with or without epidermal ectoderm derived from E 10 rat embryos. Rat epidermal ectoderm was used in these conjugate assays since the epidermal ectoderm itself expresses BMP-4 (Liem, 1995). Neural plate explants grown alone expressed only a low level of BMP-4 whereas explants grown in contact with rat epidermal ectoderm were induced to express a high level of BMP-4 (FIG. 9B). Recombinant BMP-4 and BMP-7 mimicked the ability of the epidermal ectoderm to induce high level BMP-4 expression in ventral neural tube explants (FIG. 9B). These results provide evidence that BMP-mediated signals from the epidermal ectoderm initiate the differentiation of roof plate cells in addition to neural crest cells in the dorsal folds of the neural plate.

The Roof Plate is a Source of Multiple BMPs

The selective expression of BMP-4 by roof plate cells taken together with studies showing that the related BMP, Dsl-1 is also expressed by the roof plate (Basler, 1993; FIG. 9E) prompted the applicants to examine whether other members of the BMP family are expressed by roof plate cells. Between stages 15–25, BMP-5 was also expressed selectively and at high levels by roof plate cells (FIG. 9D). In addition, BMP-7 expression was detected at high levels in the roof plate between stages 18 and 26 with lower levels of expression detected in cells in the ventricular zone of the dorsal spinal cord (FIG. 9E). In contrast, BMP-2 was not expressed by roof plate cells or other cells in the spinal cord at these embryonic stages (FIG. 9C). Thus, roof plate cells express at least four members of the BMP family over the period that classes of interneurons in the dorsal neural tube are generated.

Expression of LIM Homeobox Genes LH-2A and LH-2B Defines a Subset of Dorsal Commissural Neurons The sequential expression of BMPs by the epidermal ectoderm and the roof plate, combined with the ability of BMPs to initiate the differentiation of roof plate cells and neural crest cells prior to neural tube closure, raised the question of whether the roof plate and its resident BMPs have a role in the differentiation of dorsal cell types generated at later stages, after the epidermal ectoderm loses contact with the neural epithelium and cease to express BMP-4 and BMP-7 (Liem, 1995). To begin to examine this question it was necessary to identify markers that define subclasses of interneurons in the dorsal region of the embryonic spinal cord. Since several members of the LIM homeobox gene family (Dawid, 1995) delineate motor neurons and certain subsets of interneurons in the ventral spinal cord (Ericson, 1992; Tsuchida, 1994; Riddle et al, 1995), it was examined whether other LIM homeobox genes might define classes of dorsal interneurons.

It was found that a subset of cells generated adjacent to the dorsal midline of the spinal cord expresses two closely-related LIM homeobox genes LH-2A and LH-2B and their encoded proteins (FIGS. 10A–H and data not shown).

These cells coexpressed the neuronal antigen Cyn-1 (FIG. 10I) and did not express msx-1/2, a marker of mitotic progenitor cells in the dorsal spinal cord (FIG. 10J) indicating that they are post-mitotic neurons. LH-2B expression was detected in these neurons from stage 19 onwards (FIGS. 10A, E) whereas LH-2A was not detected until stage 20–21 (data not shown). By stage 22, the number of LH-2B and LH-2A cells had increased and they were still restricted to the dorsal-most region the spinal cord, adjacent to the roof plate (FIGS. 10B, F). From stage 22 onwards, the pattern of expression of LH-2B and LH-2A mRNA and LH-2A/B protein was very similar (data not shown) and these cells were simply referred to as LH-2$^+$. From stage 24–27 there was a progressive ventral displacement of LH-2$^+$ (FIGS. 10C–H) and by stage 35 most LH-2$^+$ cells were located in the deep laminae of the dorsal spinal cord (data not shown). Thus, it is likely that LH-2$^+$ interneurons are generated dorsally, adjacent to the roof plate, and migrate ventrally to their final settling position in the deep dorsal horn (Langman, 1970; Hollyday, 1977). This spatial and temporal expression of LH-2A and B was conserved at all rostrocaudal levels of the spinal cord (FIG. 8J and not shown). At all stages examined LH-2 expression defined a neuronal subpopulation in the dorsal spinal cord distinct from those that expressed Isl-1 or Lim-1/Lim-2 (FIGS. 10K–N). Isl-1+ dorsal interneurons were generated over approximately the same time period as LH-2$^+$ neurons but initially occupied a more medial and ventral position in the dorsal spinal cord (FIG. 8) and later populated deeper laminae in the dorsal horn (FIG. 10M).

One class of interneurons that is generated dorsally, close to the roof plate, projects axons ventrally to cross the midline at the floor plate (Holley, 1987; Oppenheim, 1988; Dodd, 1988). These commissural neurons can be defined by expression of the axonal glycoprotein TAG-1/axonin-1 (Dodd, 1988). At stages 22–23 most LH-2A/B$^+$ cells expressed TAG-1/axonin-1 immunoreactivity on their surface (FIG. 10O, data not shown) indicating that they are commissural neurons. However, TAG-1/axonin-1$^+$ neurons were also found in regions of the dorsal spinal cord ventral to LH-2$^+$ cells (FIG. 1) indicating that LH-2 expression defines a subset of dorsally-generated commissural neurons. The most mediodorsal LH-2$^+$ cells which did not express TAG-1/axonin-1 are likely to represent the most recently generated neurons that have not yet begun to express TAG-1/axonin-1. By contrast, dorsal Isl-1$^+$ interneurons did not express TAG-1/axonin-1 (FIG. 2) and are therefore likely to be ipsilaterally projecting (association) neurons.

Figures 11A, 11B:
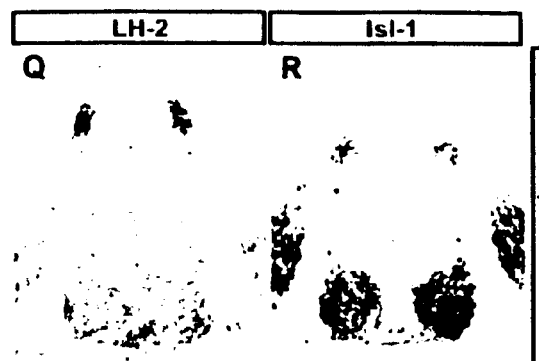
Figures 11C, 11D:

The Differentiation of LH-2$^+$ Neurons is Suppressed by Notochord-Derived Signals To determine whether LH-2$^+$ neurons are dorsal in character as well as by position, their sensitivity to notochord-derived signals was assayed. Chick notochord grafts placed adjacent to the dorsal neural tube of stage 10 host embryos completely suppressed the generation of LH-2$^+$ interneurons in the dorsal spinal cord when assayed 72 h later (FIGS. 11A, B, similar results were obtained for LH-2$^+$ mRNA; data not shown). In the same embryos, Isl-1/Isl-2$^+$ motor neurons were usually generated at ectopic dorsal positions (FIGS. 11C, D). However, complete suppression of LH-2 expression was also observed in embryos in which there was only a minimal change in the pattern of Isl-1$^+$/Isl-2$^+$ cells (data not shown) indicating that the differentiation of LH-2$^+$ interneurons is highly sensitive to repression by notochord-derived signals.

Previous studies have proposed that notochord-derived signals do not repress the differentiation of commissural neurons (Artinger, 1992). In contrast, the present studies show that the differentiation of LH-2$^+$ dorsal commissural neurons is repressed by a notochord-derived signal. These results, taken together with previous findings that notochord grafts suppress the expression of early molecular markers of dorsal neural tube cells (Yamada, 1991; Goulding, 1993; Basler, 1993) and markedly decrease the number of neural crest cells (Liem, 1995) indicate that a notochord-derived signal, presumably SHH, can subvert the dorsal fates of most or all cells normally generated in the dorsal neural tube.

Figures 11E, 11F:
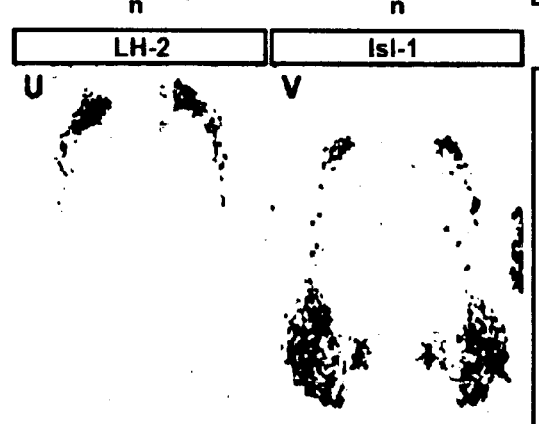
Figures 11G, 11H:

Notochord Removal Does not Alter the Position at which LH-2$^+$ Neurons are Generated Early elimination of the notochord results in the ectopic ventral expression of several markers that are normally confined to proliferating cells in dorsal neural tube (Yamada, 1991; Ericson, 1992; Basler, 1993; Goulding, 1993). This change in the pattern of cell differentiation appears to result in at least in part from the loss of a SHH-mediated repressive activity which inhibits the expression of genes from cells in medial prospective ventral regions of the neural plate (Liem, 1995). To determine whether the position at which dorsal sensory interneurons are generated is also determined in part by notochord-derived repressive signals, segments of the notochord underlying the caudal neural plate were removed from stage 10 embryos (Yamada, 1991). The effectiveness of notochord removal was established by the absence of floor plate differentiation as assessed by expression of the FP1 marker (FIGS. 11I, J) and motor neuron differentiation as assessed by Isl-1/Isl-2 (FIGS. 11G, H). At the same segmental levels LH-2$^+$ interneurons were present and more importantly were still restricted to the extreme dorsal region of the spinal cord, close to the roof plate (FIGS. 11E, F). Thus, notochord removal eliminates ventral cell types and permits the uniform dorsoventral expression of markers of proliferating dorsal cells but does not alter the position at which LH-2$^+$ commissural interneurons are generated. Similarly, after notochord removal the dorsal Isl-1$^+$ interneuron population was also detected in a dorsal position, just below LH-2$^+$ neurons, consistent with the relative position of these two classes of interneurons in normal spinal cord development (FIGS. 11G, H).

Roof Plate-Derived Signals Induce LH-2$^+$ Neurons in Vitro.

The generation of LH-2$^+$ neurons adjacent to the combined with the maintenance of their position following notochord removal led the applicants to examine whether signals derived from the roof plate are involved in inducing the local differentiation of LH-2$^+$ interneurons.

An in vitro assay of neuronal differentiation in chick neural plate explants was used to examine the differentiation of LH-2$^+$ interneurons. Explants were isolated from regions of the neural plate fated to give rise to dorsal, intermediate and ventral regions of the neural tube (Yamada, 1993; Liem, 1995) and maintained in vitro for 48 h. Cells in dorsal neural plate explants grown in vitro generated LH-2$^+$ neurons (FIGS. 11A–C). Isl-1$^+$/Isl-2$^-$ interneurons (FIGS. 12D, G) and Lim-1$^+$/Lim-2$^+$ interneurons. LH-2$^+$ interneurons were first detected in these explants after ~36 h in vitro. Intermediate neural plate explants did not generate LH-2$^+$ interneurons or Isl-1$^+$/Isl-2$^-$ interneurons but did generate Lim-1$^+$/Lim-2$^+$ interneurons (FIG. 12K). Ventral neural plate explants did not generate LH-2$^+$ interneurons, but did generate Isl-1$^+$ /Isl-2$^+$ motor neurons and Lim-1/Lim-2$^+$ interneurons (FIGS. 12I, L). Thus, explants isolated from prospective dorsal, intermediate and ventral regions of the neural plate therefore generate distinct neuronal subclasses in vitro.

The absence of LH-2$^+$ interneurons in ventral and intermediate neural plate explants grown alone in vitro permitted the examination of whether signals from the roof plate could induce the differentiation of this class of interneurons. Roof plate tissue was dissected from stage 20 and stage 24 quail embryos and grown in contact with chick intermediate or ventral neural plate explants for 48 h. LH-2$^+$ neurons were induced in ventral neural plate explants by roof plate tissue (FIGS. 12A–C) but not by neural tissue derived from the intermediate or ventral region of the spinal cord (data not shown). LH-2$^+$ neurons were detected in stage 24 quail inducing tissue indicating that the roof plate contains little or no contaminating dorsolateral tissue. Quail roof plate tissue also induced the differentiation of Isl-1$^+$/Isl-2$^-$ interneurons in intermediate neural plate explants (data not shown). Thus, roof plate cells secrete a factor or factors that can induce the differentiation of LH-2$^+$ interneurons in neural plate explants.

BMPs Mimic the Roof Plate Induction of LH-2$^+$ Interneurons

To examine whether BMPs mediate the inductive activity of the roof plate, three BMPs that are expressed by roof plate cells at relevant developmental stages, BMP-4, BMP-7 and Dsl-1 were tested for their ability to induce LH-2$^+$ neurons in ventral neural plate explants. BMP-4, BMP-7 and recombinant Dsl-1 each induced LH-2$^+$ interneurons in intermediate and ventral neural plate explants. In control experiments, condition medium from cells transfected with a truncated Dsl-1 construct failed to induce LH-2$^+$ interneurons. Thus, BMPs expressed by the roof plate mimic the ability of the roof plate cells to induce LH-2$^+$ interneurons in vitro.

Induction of Distinct Dorsal Cell Types is not Achieved at Different BMP Concentration Thresholds The results described above, raise the issue of what mechanisms determine whether roof plate cells, neural crest cells or dorsal commissural neurons are generated in neural plate explants exposed to BMPs? One possibility, by analogy with inductive events in the ventral neural tube, is that different BMP concentration thresholds are required for the induction of dorsal cell types.

To test this possibility, intermediate neural plate explants were exposed to different concentrations of BMP-4 and compared the threshold concentrations required for the induction of roof plate cells, neural crest cells (assayed by expression of the zinc finger protein slug and by the emigration of HNK-1$^+$ cells) and dorsal sensory interneurons. All three cell types were induced at the same threshold concentration and over a similar BMP-4 concentration range. Thus, the generation of cell types are not determined by the concentration of BMP signal to which neural plate cells are exposed.

A Temporal Switch in the BMP-Induced Fate of Neural Plate Cells.

The marked difference in the time of onset of differentiation of roof plate cells neural crest cells and dorsal commissural neurons raises an alternative possibility that the generation of the distinct dorsal cell type in response to BMPs might be achieved through a temporal switch in the response of neural plate cells to the same BMP signal. Specifically, progenitor cells found in the neural plate might respond to ectodermally-derived BMPs with the generation of roof plate cells and neural crest cells whereas the progenitor cells that are present dorsally at stages after neural tube closure might respond to the same concentration BMP signal derived from the roof plate with the generation of LH-2$^+$ interneurons.

To test this idea, stage 10 ventral neural plate explants were isolated and exposed them to BMP-4 continuously for 24 h, at which point the differentiation of roof plate cells, neural crest cells and dorsal sensory interneurons was assayed. After 24 h exposure to BMP-4, roof plate differentiation was detected (assayed by BMP-4 expression), premigratory (slug$^+$) cells and migratory (HNK-1$^+$) neural crest cells were generated by LH-2$^+$ interneurons were not generated (FIG. 14). Thus, early neural plate progenitors appear to have capacity to generate roof plate cells and neural crest cells in response to BMP-4. Ventral neural plate explants were grown in the absence of BMP-4 for 24 h at which point BMP-4 was added for the following 24 h. When assayed 48 h after the onset of culture, these explants did not contain neural crest cells but did contain many LH-2$^+$ interneurons. This results suggest that progenitor cells in the neural plate rapidly lose the competence to respond to a BMP-mediated signal with the generation of neural crest cells and that they instead acquire the ability to generate LH-2$^+$ interneurons.

A period of about 24 h elapses between the time that prospective dorsal neural plate cells lose contact with the epidermal ectoderm and the time that the first LH-2$^+$ neurons differentiate. Thus, the apparent inability of early neural plate progenitors to respond to BMPs with the generation of LH-2$^+$ interneurons provides important evidence that signals from the epidermal ectoderm do not have a direct role in the induction of the LH-2$^+$ neurons. The differentiation of LH-2$^+$ dorsal commissural neurons is therefore more likely to be induced by BMPs derived from roof plate cells.

Experimental Discussion

The dorsal region of the neural tube is populated by three major cell types, dorsal midline roof plate cells, premigratory neural crest cells and dorsal sensory interneurons. These cell types are generated at distinct times and appear at different positions. This study examines the origin and molecular identity of inductive signals that trigger the differentiation of these dorsal cell types and the mechanisms that regulate the time and position at which each cell type is generated. The differentiation of roof plate cells appears to be initiated prior to neural tube closure by a BMP-mediated signal from the adjacent epidermal ectoderm in a process similar to that implicated previously in the induction of neural crest cell differentiation. In contrast, the differentiation of a subset of dorsal commissural neurons appears to be initiated after neural tube closure in response to a local inductive signal from the roof plate. This roof plate derived signal, however, also appears to be mediated by BMPs, including those secreted by the epidermal ectoderm at an earlier stage of development.

How then, are distinct dorsal cell identities established in response to a quantatively similar inductive signal? Our results suggest that the distinct identities of roof plate cells, neural crest cells and dorsal commissural neurons are not established through the ability of BMPs to confer distinct dorsal cell fates at different concentration thresholds. The results suggest that instead, the decision of neural progenitors to differentiate into neural crest cells or dorsal commissural neurons is influenced by a temporal switch in the response of neural progenitors to a similar or identical BMP signal. Thus, the time at which a progenitor cell is exposed to a BMP-mediated signal is a critical determinant of its eventual fate. It is proposed that exposure of dorsal progenitors at neural plate and early neural tube stages to a BMP signal initiates neural crest differentiation whereas exposure of dorsal progenitors at later stages to the same BMP signal leads to the generation of dorsal commissural interneurons. These results raise the possibility that the principles and mechanisms used to pattern cell types in the dorsal neural tube differ significantly from those that operate in the ventral neural tube, where the concentration of inductive signal is an important determinant of ventral cell fate.

Roof Plate Induction by BMP-mediated Signals from the Epidermal Ectoderm

Roof plate cells differentiate at the dorsal midline of the neural tube and exhibit several specialized morphological, biochemical and functional properties. Analysis of the normal and induced expression of BMP-4 a selective marker of roof plate differentiation, shows that the specification of roof plate fate is initiated prior to closure of the neural tube, and apparently involves a contact-dependent signal from the adjacent epidermal ectoderm. This ectodermal signal is mimicked by two BMPS, BMP-4 and BMP-7, that are expressed in the epidermal ectoderm prior to neural tube closure (Liem, 1995). These results provide evidence that the differentiation of roof plate cells in addition to neural crest cells (Liem, 1995) is initiated by a BMP-mediated signal.

The expression of BMP-4, BMP-5, BMP-7 and Dsl-1 by roof plate cells also indicates that the establishment of dorsal midline cell fates within the neural tube involves a homeogenetic inductive process initiated by adjacent non-neural cells. The differentiation of floor plate cells at the ventral midline of the neural tube mediated by SHH (Placzek, 1995) involves a contact-dependent homeogenetic inductive signal from underlying notochord cells. Despite differences in inductive factors, the strategy used to establish the fates of cells at the dorsal and ventral midline of the neural tube is conserved.

The differentiation of neural crest cells from neural plate progenitors is also triggered prior to neural tube closure by a BMP-mediated signal from the epidermal ectoderm (Liem, 1995). There does not appear to be any difference in the threshold concentration of BMP sufficient to elicit the differentiation of these two cell types. This raises the issue of how roof plate cells and neural crest cell acquire their distinct identities. Two markers of premigratory neural crest cells, slug and cadherin 6B are expressed by cells at the dorsal midline of the neural tube as well as by cells in a more dorsolateral position. Moreover, studies of transgenic mice expressing lacZ under the control of Wnt-1 roof plate element that confers roof plate expression, promoter constructs have provided evidence that cells at the dorsal midline of the spinal cord can give rise to migratory neural crest cells. Thus, neural crest cells and roof plate cells may initially derived from the same population of dorsal midline cells. One possibility is that the selection of a roof plate as opposed to neural crest cell fate results from differences in the duration of exposure of neural plate progenitors to BMPs. Indeed, soon after neural tube closure, BMP-4 expression is retained by dorsal midline ectodermal cells at stages after more lateral ectodermal cells have ceased expressing the gene (Liem, 1995) and thus, dorsal midline neural tube may be expressed to a more prolonged ectodermally-derived BMP signal.

Induction of LH-2$^+$ Commissural Neurons by BMP-Mediated Signals from the Roof Plate The possibility that roof plate cells might have a role in the differentiation of dorsal interneurons emerged from the analysis of the origin and timing of differentiation of LH-2$^+$ commissural interneurons. This subset of interneurons differentiated adjacent to the roof plate from stage 19 onwards, and the dorsomedial position of origin of these neurons is not affected by elimination of ventralizing signals from the notochord. Direct evidence in support of this idea derives from in vitro studies showing that roof plate tissue is able to induce LH-2$^+$ interneurons in intermediate or ventral regions of the neural plate. BMPs are strong candidates as mediators of the roof plate-derived signal that induces LH-2A/B$^+$ interneurons. Four different members of this family of secreted factors, BMP-4, BMP-5, BMP-7 and Dsl-1 are expressed at high levels by the roof plate over the period that LH-2$^+$ interneurons are generated in adjacent dorsal neuroepithelial cells. Moreover, three of these factors, BMP-4, BMP-7 and Dsl-1 mimic in vitro the ability of the roof plate to induce LH-2A/B$^+$ interneurons.

Roof plate tissue was more effective at inducing LH-2$^+$ interneurons than was any single BMP. The coexpression of at least four BMPs in roof plate cells raises the possibility that BMP heterodimers with greater inductive potency than individual BMP homodimers roof plate cells normally secrete. Indeed, BMP-4/BMP-7 heterodimers exhibit greater inductive potency than either homodimer on several non-neural cell types (Hazama, 1995; Aono, 1995). Alternatively, it remains possible that roof plate cells may secrete distinct factors that potentiate the inductive activities of BMPs. One line of evidence that the roof plate is a source of other inductive factors is suggested by the observation that BMPs are not able to mimic the ability of the roof plate to induce the subset of dorsal Isl-1+/Isl-2− interneurons in neural plate explants (KL and TMJ, unpublished observations).

BMPs are, however, expressed in the epidermal ectoderm prior to neural tube closure, raising the issue of whether epidermal ectoderm or roof plate cells represent the source of BMPs relevant for the initial induction of LH-2+ dorsal commissural neurons. It could be argued, for example, that BMPs secreted by the epidermal ectoderm prior to roof plate differentiation have a critical early role in triggering the differentiation of LH-2+ commissural neurons in much the same way that early SHH-mediated signals from the notochord trigger motor neuron differentiation prior to an independent of a secondary floor plate-derived source of SHH (Yamada, 1993).

A strong argument against this possibility is however provided by the observation that neural plate explants, isolated at a time when the neural plate is still in contact with the epidermal ectoderm, are initially not able to generate LH-2+ interneurons in response to BMP-mediated signals and acquire this capacity only after ~24 h. If the capacity of neural plate cells to generate LH-2A/B+ interneurons is acquired over the same time interval in vivo, the epidermal ectoderm would have long since separated from the neural tube and thus no longer be in a position to influence dorsal cell fates. Thus, it is likely that by the time that progenitors in the dorsal neural tube attain the competence to generate LH-2A/B+ interneurons, the roof plate is the most prominent local source of BMPs. It is considered therefore, that the roof plate to be the most likely source of signals involved in the induction of LH-2A/B+ commissural neurons.

A Developmental Switch in the Potential of Neural Plate Cells Defines the Dorsal Cell Type Induced by BMP-Mediated Signals.

BMP-mediated signals appear to be responsible both for the early induction of roof plate and neural crest cells and the later induction of LH-2A/B+ interneurons. This raises the issue of how the distinct fates of two dorsal cell types, neural crest cells and dorsal commissural neurons that are generated at similar dorsoventral positions are determined. The in vitro results provide evidence that neural plate cells change their response properties over time with the consequence that cell types induced in response to the same concentration of a single BMP differ at distinct stages. Thus, neural plate cells exposed immediately to BMPs generate roof plate cells and neural crest cells but not LH-2+ interneurons whereas equivalent explants that have been matured in vitro in the absence of an exogenous source of BMP lose the ability to generate roof plate and neural crest cells and acquire the ability to generate dorsal commissural neurons.

These findings suggest that a temporal change in the competence of neural plate cells to BMPs establishes the temporal order and spatial pattern of cell types generated in the dorsal neural tube. In this model, BMP-mediated signals from the epidermal ectoderm act on immature neural progenitors to induce both roof plate cells and neural crest cells. Once induced, neural crest cells emigrate from the dorsal neural tube, and thus expose more mature dorsal neural progenitors to the effects of roof plate-derived BMPs, resulting in the generation of LH-2+ interneurons in the region close to the roof plate.

Materials and Methods
Isolation of a Chick LH-2B cDNA Clone $6\times10^5$ plaques of an adult chick brain cDNA lambda gt 11 library (Clontech) have been plated out and screened at high stringency with a $^{32}$P random labeled (Stratagene) probe derived from a rat LH-2 cDNA clone (Xu et al., 1993) cut with Xba/EcRI.

The inserts of 10 isolated cDNA's were subcloned into the KS bluescript vector and clone LH-6.1 was sequenced on both strands (Sequenase 2.0, United Stages Biochemicals) Despite the low sequence homology at the 3' end between the chick and the rat LH-2, two lines of evidence suggest that the isolated chick cDNA encodes the most abundant LH-2 transcript. First, RNA protection experiments on RNA isolated from chick embryonic brain and limb using a probe from the 3' region of the cDNA revealed one single protected fragment, suggesting that no alternative splicing is occurring at the 3' end. Second, the sequences of cloned RT-PCR products derived from different RNA's such as brain, spinal cord, and limb RNA isolated from embryonic (E) 4.5 chick tissue were identical to the sequences cloned from the cDNA library.

Production of the bacterial fusion protein and Generation of an antiserum

A 430 bp Hind2/SmaI fragment spanning the homeodomain and the C-terminal end of the chick LH2 cDNA was ligated into the SmaI site of the pGEX 3X Glutathione S-transferase Gene Fusion Vector (Pharmacia). The construct was introduced into the *E. coli* strain BL21(DE3) (Studier, 1986). The 45–46 kd fusion protein (as estimated based on the mobility in SDS-polyacrylamide gels) was purified from bacterial lysates by affinity chromatography using glutathione crosslinked agarose beads (Smith, 1988).

Rabbits were subcutaneously injected with an emulsion containing 1 part of antigen (400 mg) and 1 part of complete Freund's adjuvant. Four injection boosts were applied at three weeks interval with Freund's incomplete adjuvant (see Harlow and Lane, 1988). The serum was collected two weeks after the last boost and absorbed against a bacterial whole cell powder (prepared as an acetone powder, Harlow and Lane, 1988) previously induced to express the Glutathione S-transferase protein. The absorbed serum was stored at 4° C. or at −80° C.

Whole Mount in Situ Hybridization

Whole mount in situ hybridization was performed with digoxigenin labelled probes according to Harland (1991) on tissue fixed with 4% paraformadelhyde. The antisense probe was generated with T3 polymerase using the full length LH-2 cDNA as a template (Boehringer). Hybridization on sections were performed on fress frozen 10 um tissue sections according to Scharen-Wiemers and Gerfin-Moser (1993) and Tsuchida et al. (1994). The hybridization signals were detected by a secondary antibody coupled to alkaline phosphatase (Boehringer) and subsequent staining with BCIP and X-phosphate. The reaction time varied from 1–4 hours. In all control hybridizations, sense probes revealed no detectable signals.

Immunohistochemistry

Embryos were fixed in 4% paraformaldehyde in 0.12M phosphate buffer for 1–2 hours on ice, washed extensively with PBS for 3–5 hours and preserved in 30% sucrose over night at 4° C. Frozen sections were collected, washed with PBS and incubated over night at 4° C. with the primary antibody at a final concentration of 1:1000 for the rabbit serum and 1:1 diluted for monoclonal antibodies in PBS, 0.1% triton X-100 and 1% serum. After rinsing with PBS the sections were incubated in secondary antibodies over night at 4° C. with HRP-conjugated goat anti rabbit (TAgo, 1:400) or goat anti mouse IgG (Tago, 1:200). For the confocal images secondary antibodies were incubated for 1 hour at room temperature with Bodipy fluorochrome goat anti rabbit IgG or goat anti mouse IgG conjugate (Molecular Probes, 1:100), Texas Red goat anti rabbit IgG conjugate or goat anti mouse IgG or IgM (molecular probes, 1:200).

Antigens recognized by monoclonal antibodies

The monoclonal antibody MAb Isl-1 (IgG) recognizes antigens specific for the whole motor neuron population (Ericson et al., 1992; Tsuchida et al., 1994). In addition, an as yet unidentified dorsal population of cells are labelled. Antigens specifically expressed in the floor plate are recognized by the MAb FP1 (IgG, Yamada et al., 1991). MAb (IgG) directed against Lim-1 cross reacts with Lim-2. (Tsuchida et al., 1994) and labels parts of the motor neuron pool in addition to interneurons intermedially localized. MAb TAG-1 (IgM) recognizes the earliest expression of the rat TAG-1 in spinal commissural neurons occurs at E11.5 and is initially confined to the cytoplasma of the cell bodies (FIG. 4b), whereas at later stages TAG-1 expression becomes restricted to axons (Dodd et al., 1988). The chick specific MAb (IgG) axonin-1/TAG-1 has been generated from mice that had been injected with chick spinal cord membranes. The antibody was identified by western blots on purified protein axonin-1 (Morton, Condon and Jessell, unpublished data) and be expression analyst in the chick spinal cord (unpublished). The MAb (IgM) cyn-1 (Morton, Tremml and Jessell, unpublished data), a side product of a fusion, recognizes an unidentified antigen localized in the cytoplasm of differentiated neurons.

Dorsal Notochord Grafts and Notochord Removals

The surgical procedures were performed according to Yamada et al., (1991). In order to obtain a dorsal grafts, notochords were inserted into the open neural tube and partially pushed rostrally into the lumen of the already closed tube at stage 10. During the process of neural tube closure the inserted notochords were pushed dorsally and caudally out of the lumen. Thus, the analysis after an incubation time of an additional 72 hours showed notochord grafts (n=5) at thoracic and lumbar levels.

Notochord removals were done essentially as described (Yamada et al., 1991), except that the operated embryos were analyzed after additional 72 hours of incubation. The operated embryos showed deletions at thoracic and lumbar levels.

REFERENCES

Artinger, K. B., and Bronner-Fraser, M. (1992) Notochord grafts do not suppress formation of neural crest cells or commissural neurons. Development 116, 877–886.

Basler, K., Edlund, T., Jessell, T., and Yamada, T. (1993) Control of cell pattern in the neural tube: regulation of cell differentiation by dorsalin-1: a novel TGFβ family member. Cell 73, 687–702.

Brand-Saberi, B., Ebensperger, C., Wilting, J., Balling, R. and Christ, B. (1993) The ventralizing effect of the notochord on somite differentiation in chick embryos. Anat. Embryol. 188, 239–245.

Dickinson, M. E., Selleck, M. A. J., McMahon, A. P. and Bronner-Fraser, M. (1995) Dorsalization of the neural tube by the non-neural ectoderm. Development 121, 2099. Echelard, Y., Epstein, D. J., St-Jacques, B., Shen, L., Mohler, J., McMahon, J. A., and McMahon, A. P. (1993). Sonic hedgehog, a member of a family of putative signaling molecules, is implicated in the regulation of CNS polarity. Cell 75, 1417–1430.

Ericson, J., Thor, S., Edlund, T., Jessell, T. M., and Yamada, T. (1992). Early stages of motor neuron differentiation revealed by expression of homeobox gene Islet-1 Science 256, 1555–1560.

Ericson, J., Muhr, J., Placzek, M., Lints, T., Jessell, T. M., and Edlund, T. (1995) Sonic hedgehog induces the differentiation of ventral forebrain neurons: a common signal for ventral patterning along the rostrocaudal axis of the neural tube. Cell 81, 747–756.

Fainsod, A. Steinbeisser, H., and de Robertis; E. M. (1994) On the function of BMP-4 in patterning the marginal zone of the Xenopus embryo. EMBO J. 13, 5015–5025.

Fan, C-M., and Tessier-Lavigne, M. (1994) Patterning of mammalian somites by surface ectoderm and notochord: evidence for sclerotome induction by a hedgehog homolog. Cell 79, 1165–1174.

Fan, C-M., Porter, J. A., Chang, C., Chang, D. T., Beachy, P. A., and Tessier-Lavigne, M. (1995) Long-range sclerotome induction by sonic hedgehog: direct role of the amino terminal cleavage product and modulation by the cyclic AMP signaling pathway. Cell 81, 457–465.

Francis, P. H., Richardson, M. K., Brickell, P. M., and Tickle, C. (1994) Bone morphogenetic proteins and a signaling pathway that controls patterning in the developing chick limb. Development 120, 209–218.

Goulding, M., Lumsden, A., and Gruss, P. (1993) Signals from the notochord and floor plate regulate the region-specific expression of two Pax genes in the developing spinal cord. Development 117, 1001–1016. Graham, A., Francis-West, P., Brickell, P. and Lumsden, A. (1994) The signaling molecule BMP-4 mediates apoptosis in the rhombencephalic neural crest. Nature 372, 684–686.

Hamburger, V., and Hamilton, H. (1951) A series of normal stages in the development of chick embryo. J. Morphol. 88, 49–92.

Houston, B., Thorp, B. H. and Burt, D. W. (1994) Molecular cloning and expression of bone morphogenetic protein 7 in the chick epiphyseal growth plate. J. Mol. Endocrinol. 13, 289–301.

Johnson, R. and Tabin, C. (1995) The long and short of hedgehog. Cell 81, 313–316.

Johnson, R. D., Laufer, E., Riddle, R. D. and Tabin, C. J. (1994) Ectopic expression of sonic hedgehog alters dorsal-ventral patterning of somites. Cell 79, 1166–1174.

Jones, C. M., Lyons, K. M., Hogan, B. L. M. (1991) Involvement of bone morphogenetic protein-4 (BMP-4) and Vgr-1 in morphogenesis and neurogenesis in the mouse. Development 111, 531–542.

Kingsley, D. The TGF-β superfamily: new members, new receptors, and new genetic tests of function in different organisms. (1994) Genes Dev. 8, 133–146.

Krauss, S., Concordet, J. P., and Ingham, P. W. (1993). A functionally conserved homolog of the Drosophila segment polarity gene hedgehog is expressed in tissues with polarizing activity in zebrafish embryos. Cell 75, 1431–1444.

Liem, K. F., Tremml, G., Roelink, H., and Jessel, T. M. (1995) Dorsal Differentiation of Neural Plate Cells Induced by BMP-mediated Signals from Epidermal Ectoderm. Cell 82, 969–979.

Lu, S., Bogarad, L. D., Murtha, M. T., and Ruddle, F. H. (1992) Expression pattern of a murine homeobox gene, Dbx, displays extreme spatial restriction in embryonic forebrain and spinal cord. Proc. Natl. Acad. Sci. USA 89, 8053–8057.

Lyons, K., Hogan, B., and Robertson, E. (1995) Colocalization of BMP7 and BMP2 RNAs suggests that these factors cooperatively mediate tissue interactions during murine development. Mechanisms of Development 50, 71–83.

Marti, E., Bumcrot, D. A., Takada, R. and McMahon, A. P. (1995) Requirement of 19K form of sonic hedgehog for induction of distinct ventral cell types in CNS explants. Nature 375, 322–325.

Martins-Green, M. (1988) Origin of the dorsal surface of the neural tube by progressive delamination of epidermal ectoderm and neuroepithelium: implications for neurulation and neural tube defects. Development, 103, 607–706.

Massague, J., Attisano, L., and Wrana, J. L. (1994) The TGF( family and its composite receptors. Trends Cell Biol. 4, 172–178.

Mayor, R., Morgan, R., and Sargent, M. (1995) Induction of the prospective neural crest of Xenopus. Development 121, 767–777.

Moury, J. and Jacobson, A. (1989) Neural fold formation at newly created boundaries between neural plate and epidermis in the axolotl. Dev. Biol. 133, 44–57.

Moury, J. and Jacobson, A. (1990) The origins of neural crest cells in the axolotl. Dev. Biol. 141, 243–253;.

Nakagawa, S., and Takeichi, M. (1995) Neural crest cell-cell adhesion controlled by sequential and subpopulation-specific expression of novel cadherins. Development 121, 1321–1332.

Nieto, A., Sargent, M., Wilkinson, D., and Cooke, J. (1994) Control of cell behavior during vertebrate development by Slug, a zinc finger gene. Science 264, 835–839.

Placzek, M., Jessell, T. M., and Dodd, J. (1993) Induction of floor plate differentiation by contact-dependent, homeogenetic signals. Development 117, 205–218.

Porter, J. A., Ekker, S. C., Young, K. E., von Kessler, D. P., Lee, J. J., Moses, K., and Beachy, P. A. (1995) The product of hedgehog autoproteolytic cleavage active in local and long-range signaling. Nature 374, 363–366.

Pourquie, O., Coltey, M., Teillet, M.-A., Ordahl, C. and Le Douarin, N. M. (1993) Control of dorso-ventral patterning of somitic derivatives by notochord and floor plate. Proc. Natl. Acad. Sci. USA 90, 5242–5246.

Rangini, Z., Ben-Yehuda, A., Shapira, E., Gruenbaum, Y., and Fainsod, A. (1991) Chox E, a chicken homeogene of the H2.0 type exhibits dorso-ventral restriction in the proliferating region of the spinal cord. Mech. of Dev. 35, 13–24.

Robert, B., Lyons, G., Simandl, B., Kuroiwa, A., and Buckingham, M. (1991) The apical ectodermal ridge regulates Hox-7 and Hox-8 gene expression in developing chick limb buds. Genes Dev. 5, 2363–2374.

Roelink, H. , Augsburger, A., Heemskerk, J., Korzh, V., Norlin, S., Ruiz i Altaba, A., Tanabe, Y., Placzek, M., Edlund, T., Jessell, T., and Dodd, J. (1994). Floor plate and motor neuron induction by vhh-1, a vertebrate homolog of hedgehog expressed by the notochord. Cell 76, 761–775.

Roelink, H., Porter, J., Chiang, C., Tanabe, Y., Chang, D. T., Beachy, P. A., and Jessell, T. M. (1995) Floor plate and motor neuron induction by different concentrations of the amino terminal cleavage product of sonic hedgehog autoproteolysis. Cell 81, 445–455.

Satokata, I., and Maas, R. (1994) Msx-1 deficient mice exhibit cleft palate and abnormalities of craniofacial and tooth development. Nature Genetics 6, 348–356.

Scherson, T., Serbedzija, G., Fraser, S., and Bronner-Fraser, M. (1993) Regulative capacity of the cranial neural tube to form neural crest. Development 118, 1049–1062.

Selleck, M., and Bronner-Fraser, M. (1995) Origins of the avian neural crest: the role of neural plate-epidermal interactions. Development 121, 525–538. Smith, J. C. (1994) Hedgehog, the floor plate, and the zone of polarizing activity. Cell 76, 193–196.

Stuart, E. T., Kioussi, C., and Gruss, P. (1994) Mammalian Pax genes. Ann. Rev. Gen. 28, 219–236. Takada, S., Stark, K., Shea, M., Vassileva, G., McMahon, J., and McMahon, A. (1994) Wnt-3a regulates somite and tailbud formation in the mouse embryo. Genes Dev. 8, 174–189.

Takahashi, Y., Monsoro-Burq, A., Bontoux, M., and Le Douarin, N. (1992) A role for Quox-8 in the establishment of the dorsoventral pattern during vertebrate development. Proc. Nat. Acad. Sci. USA 89, 10237–10241.

Tanabe, Y, Roelink, H, and Jessell, T. M. (1995) Induction of motor neurons by sonic hedgehog is independent of floor plate differentiation. Current Biology 5, 651–658.

Trueb, B., Schreier, T., Winterhalter, K., and Strehler, E. (1988) Sequence of a cDNA clone encoding chicken ribosomal protein S17. Nucleic Acids Res. 16, 4723.

Tucker, G., Aoyama, H., Lipinski, M., Tursz, T., and Thiery, J. (1984) Identical reactivity of monoclonal antibodies HNK-1 and NC-1: conservation in vertebrates on cells derived from the neural primordium and on some leukocytes. Cell. Diff. 14, 223–230.

Vainio, S., Karavanova, I., Jowett, A., and Thesleff, I. (1993) Identification of BMP-4 as a signal mediating secondary induction between epithelial and mesenchymal tissues during early tooth development. Cell 75, 52–58. van Straaten, H. M. W., and Hekking, J. W. M. (1991) Development of floor plate, neurons and axonal outgrowth pattern in the early spinal cord of the notochord-deficient chick embryo. Anat. Embryol. 184, 55–63.

Yamada, T., Placzek, M. Tanaka, H., Dodd, J., and Jessell, T. M. (1991). Control of cell pattern in the developing nervous system: polarizing activity of the floor plate and notochord. Cell 64, 635–647. Yamada, T., Pfaff, S., Edlund, T., and Jessell, T. (1993) Control of cell pattern in the neural tube: motor neuron induction by diffusible factors from notochord and floor plate. Cell 73, 673–686.

Yokouchi, Y., Ohsugi, K., Sasaki, H., and Kuroiwa, A. (1991) Chicken homeobox gene Msx-1: structure, expression in limb buds and effect of retinoic acid. Development 113, 431–444.

Zimmerman, K., Shih, J., Bars, J., Collazo, A., and Anderson, D. J., (1993) Xash-3, a novel Xenopus achaete-scute homolog, provides an early marker of planar neural induction and position along the mediolateral axis of the neural plate. Development 119, 221–232.

What is claimed is:

1. A method for stimulating neural crest cell differentiation in vitro comprising contacting a neural plate progenitor cell with a composition, which composition comprises an amount of bone morphogenetic protein 5 effective to stimulate neural crest cell differentiation and an acceptable carrier, thereby stimulating neural crest cell differentiation.

* * * * *